United States Patent
Bien et al.

(10) Patent No.: US 11,707,211 B2
(45) Date of Patent: Jul. 25, 2023

(54) IMPLANTABLE SENSOR DRIVEN BY ALIGNMENT KEY, IMPLANTABLE DEVICE COMPRISING IMPLANTABLE SENSOR, AND BIOMETRIC DATA MEASUREMENT SYSTEM COMPRISING IMPLANTABLE DEVICE

(71) Applicant: UNIST (ULSAN NATIONAL INSTITUTE OF SCIENCE AND TECHNOLOGY), Ulsan (KR)

(72) Inventors: Franklin Don Bien, Ulsan (KR); Gang Il Byun, Ulsan (KR)

(73) Assignee: UNIST (Ulsan National Institute of Science and Technology)

(*) Notice: Subject to any disclaimer, the term of this patent is extended or adjusted under 35 U.S.C. 154(b) by 0 days.

(21) Appl. No.: 18/059,406

(22) Filed: Nov. 28, 2022

(65) Prior Publication Data
US 2023/0092592 A1    Mar. 23, 2023

Related U.S. Application Data

(63) Continuation of application No. PCT/KR2021/006506, filed on May 25, 2021.

(30) Foreign Application Priority Data

May 27, 2020  (KR) ................. 10-2020-0063815
May 14, 2021  (KR) ................. 10-2021-0062699

(51) Int. Cl.
*A61B 5/145*    (2006.01)
*A61B 5/06*     (2006.01)
*A61B 5/00*     (2006.01)

(52) U.S. Cl.
CPC ........ *A61B 5/14503* (2013.01); *A61B 5/0031* (2013.01); *A61B 5/062* (2013.01);
(Continued)

(58) Field of Classification Search
CPC ... A61B 5/14503; A61B 5/0031; A61B 5/062; A61B 5/14532; A61B 5/6847; A61B 2560/0219; A61B 2562/166
See application file for complete search history.

(56) References Cited

U.S. PATENT DOCUMENTS 6,958,735 B2 * 10/2005 Handelsman .......... H01Q 11/18
                                                    343/742
7,215,292 B2 *  5/2007 McLean .................. H01Q 9/28
                                                    343/726
(Continued)

FOREIGN PATENT DOCUMENTS

CN      110300546 A    10/2019
JP       4745833 B2     8/2011
(Continued)

OTHER PUBLICATIONS

International Preliminary Report on Patentability (Incorporating PCT Written Opinion) dated Nov. 17, 2022, as issued in corresponding International Application No. PCT/KR2021/006506, filed May 25, 2021, 10 pages.

(Continued)

*Primary Examiner* — Eric J Messersmith
(74) *Attorney, Agent, or Firm* — Christensen O'Connor Johnson Kindness PLLC

(57) ABSTRACT

Disclosed are an implantable sensor driven by an alignment key, an implantable device comprising the implantable sensor, and a biometric data measurement system comprising the implantable device. The implantable device according to the present embodiment may comprise an implantable sensor forming a magnetic dipole moment in one direction from the inside to the outside of the body, and may be inserted into the body to measure biometric data by means of the implantable sensor.

13 Claims, 29 Drawing Sheets

(52) U.S. Cl.
CPC ........ *A61B 5/14532* (2013.01); *A61B 5/6847* (2013.01); *A61B 2560/0219* (2013.01); *A61B 2562/166* (2013.01)

(56) References Cited

U.S. PATENT DOCUMENTS

| | | |
|---|---|---|
| 9,387,331 B2 | 7/2016 | Zhao et al. |
| 11,026,603 B2 * | 6/2021 | Omenetto ............ A61B 5/1468 |
| 2017/0001003 A1 | 1/2017 | Pivonka et al. |
| 2019/0116433 A1 * | 4/2019 | Hesselballe ............ H01Q 1/273 |
| 2020/0015722 A1 | 1/2020 | Vesali et al. |

FOREIGN PATENT DOCUMENTS

| | | |
|---|---|---|
| KR | 10-0856507 B1 | 9/2008 |
| KR | 10-2185556 B1 | 12/2020 |

OTHER PUBLICATIONS

Written Opinion dated Sep. 6, 2021, issued in corresponding International Application No. PCT/KR2021/006506 filed May 25, 2021, 6 pages.

* cited by examiner

<Folded single loop>

Folding line

<Folded double loop>

Constructive interference!

Implantable sensor

External sensor

IMPLANTABLE SENSOR DRIVEN BY ALIGNMENT KEY, IMPLANTABLE DEVICE COMPRISING IMPLANTABLE SENSOR, AND BIOMETRIC DATA MEASUREMENT SYSTEM COMPRISING IMPLANTABLE DEVICE

CROSS-REFERENCE TO RELATED APPLICATION(S)

This application is bypass continuation of International Application No. PCT/KR2021/006506, filed May 25, 2021, which claims the benefits of Korean Patent Application No. 10-2020-0063815, filed on May 27, 2020, and Korean Patent Application No. 10-2021-0062699, filed on May 14, 2021, in the Korean Intellectual Property Office, the disclosures of Which is herein incorporated by reference in their entireties.

TECHNICAL FIELD

Embodiments are related to an implantable sensor driven by an alignment key, an implantable device including the implantable sensor, and a system for measuring biometric information including the implantable device.

BACKGROUND OF THE DISCLOSURE

Cases in which adult-onset diseases, such as diabetes, hyperlipidemia, and thrombosis, are increased are continuously reported. Since it is important to continuously monitor and manage such diseases, the diseases need to be periodically measured by using various bio sensors. A common type of a bio sensor is a method of injecting blood gathered from a finger into a test strip and then quantizing an output signal by using an electrochemical method or a photometry method. Such an approach greatly torments a user because blood needs to be gathered each time.

If an invasive method is used, there is a method of measuring biometric information by inserting an implantable sensor into the skin, measuring, the biometric information for a given time, and making the measured information read by an external reader. In this case, in order for the external reader to collect biometric information measured by the implantable sensor, the location of the implantable sensor inserted into the skin needs to be accurately checked.

The aforementioned information is merely for helping understanding, may include contents which do not form a part of the conventional technology, and may not include contents which may be presented to those skilled in the art through the conventional technology.

SUMMARY

Provided are a system and method for measuring biometric information, which can accurately measure biometric information by measuring a characteristic change attributable to a change in the analyte through an implantable device and an external device.

Provided are an implantable sensor driven by an alignment key so that an external device outside the body can accurately check the location of an implantable device within the body, and the implantable device including the implantable sensor.

There is provided an implantable device including an implantable sensor configured to form a magnetic dipole moment in one direction outside an body within the body, wherein the implantable device is inserted into the body and measures biometric information by using the implantable sensor.

According to an aspect, the implantable sensor may have a triple folded loop structure in which one port feeding and a folded double loop have been merged.

According to another aspect, the port feeding and the folded double loop may be merged to form magnetic dipole resonance through single feeding.

According to still another aspect, in the implantable device, a current at the top of the triple folded loop structure and a current at the bottom of the triple folded loop structure may be offset to form sub-radiative resonance by a vertical symmetry shape of the triple folded loop structure.

According to still another aspect, a first side of the port feeding may be connected to a first side at the top of a, first folded loop of the folded double loop, a second side of the port feeding may be connected to a first side at the top of a second folded loop of the folded double loop, and a second side at the bottom of the first folded loop and a second side at the bottom of the second folded loop may be connected.

According to still another aspect, the triple folded loop structure may be implemented in a printed circuit board (PCB).

According to still another aspect, the implantable device may further include a power source for applying a current to the implantable sensor. A current may be induced into an external sensor outside the body, which has a loop structure, by a magnetic field that is formed by a current applied from the power source to the implantable sensor. A location of the implantable sensor may be determined based on a size of the current induced into the external sensor.

According to still another aspect, the implantable sensor may have a triple folded loop structure having an oval structure. A direction of the implantable sensor may be determined based on a size of a current induced into an external sensor outside the body, which has a loop structure of an oval structure.

According to still another aspect, the biometric information may be measured based on a change in magnetic dipole moment resonance according to a change in permittivity.

There is provided an implantable sensor having a triple folded loop structure in which one port feeding and a folded double loop have been merged.

According to an aspect, the port feeding and the folded double loop may be merged to form magnetic dipole resonance through single feeding.

According to another aspect, a current at the top of the triple folded loop structure and a current at the bottom of the triple folded loop structure may be offset to form sub-radiative resonance by a vertical symmetry shape of the triple folded loop structure.

According to still another aspect, a first side of the port feeding may be connected to a first side at the top of a first folded loop of the folded double loop. A second side of the port feeding may be connected to a first side at the top of a second folded loop of the folded double loop. A second side at the bottom of the first folded loop and a second side at the bottom of the second folded loop may be connected.

According to still another aspect, each of the port feeding and the folded double loop may have an oval shape.

There is provided a system for measuring biometric information, wherein biometric information may be able to be measured by measuring a characteristic change according to a change in an analyte through an implantable device and an external device, the implantable device includes an implantable sensor configured to form a magnetic dipole moment in one direction outside an body within the body, the implantable device is inserted into the body and measures the biometric information by using the implantable sensor, and the external device transfers power for driving the implantable device and generates data for the biometric information by using digital data transferred by the implantable device.

Biometric information can be accurately measured by measuring a characteristic change attributable to a change in the analyte through the implantable device and the external device.

The external device outside the body can accurately check the location of the implantable device within the body.

DETAILED DESCRIPTION

Figure 1:
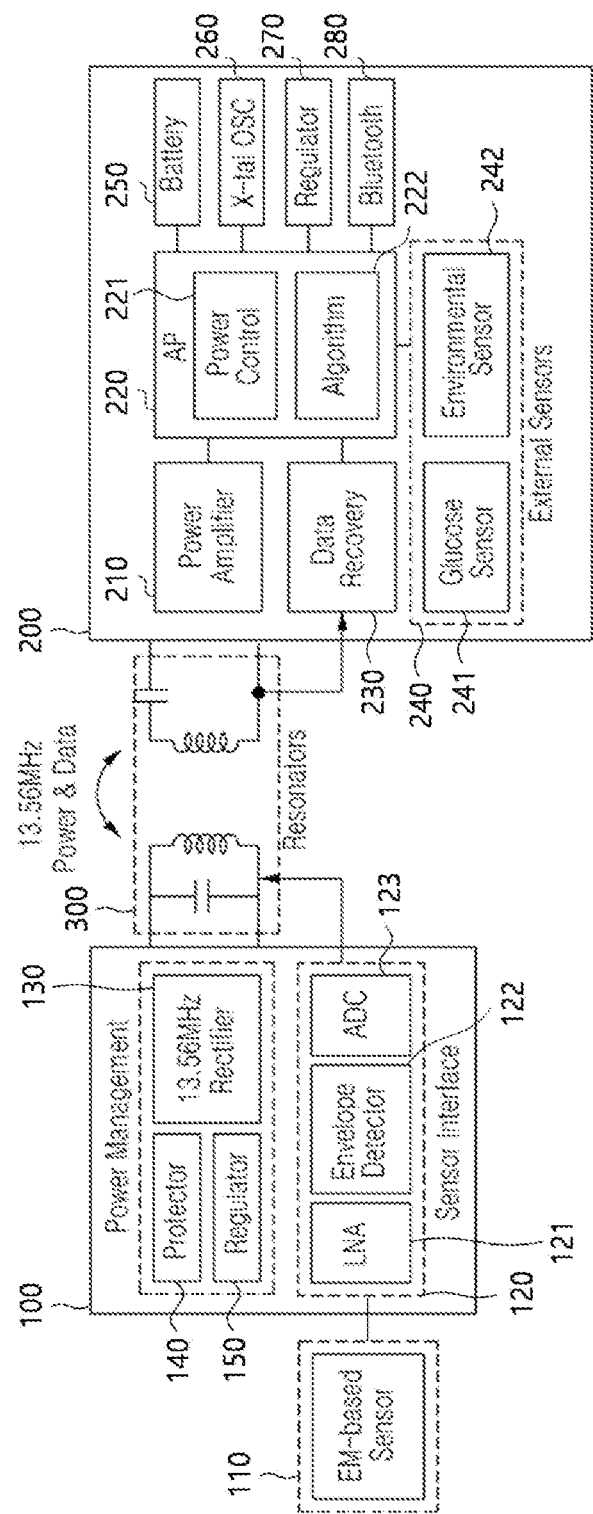
FIG. 1 is a diagram illustrating an example of a system for measuring biometric information according to an embodiment of the present disclosure.

Hereinafter, embodiments are described in detail with reference to the accompanying drawings. However, the embodiments may be changed in various ways, and the scope of right of this patent application is not limited or restricted by such embodiments. It is to be understood that all changes, equivalents and substitutions of the embodiments are included in the scope of right.

Terms used in embodiments are merely used for a description purpose and should not be interpreted as intending to restrict the present disclosure. An expression of the singular number includes an expression of the plural number unless clearly defined otherwise in the context. In this specification, it should be understood that a term, such as "include" or "have", is intended to designate the presence of a characteristic, a number, a step, an operation, a component, a part or a combination of them described in the specification, and does not exclude the existence or possible addition of one or more other characteristics, numbers, steps, operations, components, parts, or combinations of them in advance.

All terms used herein, including technical or scientific terms, have the same meanings as those commonly understood by a person having ordinary knowledge in the art to which an embodiment pertains, unless defined otherwise in the specification. Terms, such as those commonly used and defined in dictionaries, should be construed as having the same meanings as those in the context of a related technology, and are not construed as being ideal or excessively formal unless explicitly defined otherwise in the specification.

Furthermore, in describing the present disclosure with reference to the accompanying drawings, the same component is assigned the same reference numeral regardless of its reference numeral, and a redundant description thereof is omitted. In describing an embodiment, a detailed description of a related known art will be omitted if it is deemed to make the subject matter of the embodiment unnecessarily vague.

Furthermore, in describing elements of an embodiment, terms, such as a first, second, A, B, (a), and (b), may be used. Such terms are used only to distinguish one component from another component, and the essence, order, or sequence of a, corresponding component is not limited by the terms. When it is said that one component is "connected", "combined", or "coupled" to another component, the one component may be directly connected or coupled to another component, but it should also be understood that a third component may be "connected", "combined", or "coupled" between the two components.

A component included in any one embodiment and a component including a common function are described using the same name in another embodiment. Unless described otherwise, a description written in any one embodiment may be applied to another embodiment, and a detailed description in a redundant range is omitted.

FIG. 1 is a diagram illustrating an example of a system for measuring biometric information according to an embodiment of the present disclosure. The system for measuring biometric information according to the present embodiment may include an implantable device 100 and an external device 200.

The implantable device 100 including an electro-magnetic (EM)-based sensor 110 fabricated to measure biometric information in an interstitial fluid is disposed under the skin, and has a characteristic in which a resonance frequency thereof is changed in response to permittivity around the implantable device 100. In order to operate the EM-based sensor 110 included in the implantable device 100, a signal whose frequency is constantly changed needs to be injected. If such a signal is changed through the EM-based sensor 110, an sensor interface 120 for measuring the changed signal is required. Furthermore, the external device 200 may predict a change (e.g., a change in the concentration of blood glucose) in biometric information of an interstitial fluid through a change in coupling intensity based on a fringing field. In this case, the accuracy of measurement of biometric information may be supplemented by using several multimodes using the implantable device 100 and the external device 200.

The implantable device 100 may include the sensor interface 120 for measuring a signal that is changed through the EM-based sensor 110, along with the EM-based sensor 110 fabricated to measure biometric information in an interstitial fluid. The sensor interface 120 may include a low-noise amplifier (INA) 121, an envelope detector 122, and an analog-digital converter (ADC) 123. Such a sensor interface 120 is more specifically described with reference to FIG. 2.

The external device 200 may transfer power to the implantable device 100 through a resonator 300. Data transmission between the implantable device 100 and the external device 200 may also be performed by using the resonator 300. The resonator 300 may induce a wave or vibration having a specific frequency by using a resonant phenomenon between a first circuit (e.g., this is an electric circuit including a coil and a condenser and is a wireless power receiver) included in the implantable device 100 and a circuit (e.g., this is an electric circuit including a coil and a condenser and is a wireless power transmitter) included in the external device 200. In the embodiment of FIG. 1, a frequency of 13.56 MHz is described as being used, but the present disclosure is not limited thereto.

In this case, the implantable device 100 may further include a rectifier 130, a protector 140, and a regulator 150 in order to manage power transferred through the resonator 300. The rectifier 130 may be used to obtain DC power from AC power that is transferred through the resonator 300. The regulator 150 may be used to maintain a constant voltage. The protector 140 is an overvoltage protector, and may be used to prevent damage to the system due to high power in the implantable device 100 when power is transmitted by the external device 200.

As illustrated in FIG. 1, the external device 200 may include a power amplifier 210, an application processor (AP) 220, a data recovery module 230, an external sensor 240, a battery 250, an X-tal oscillator (USC) 260, a regulator 270, and a Bluetooth module 280. The external sensor 240 may include an EM-based glucose sensor 241 that enables the external device 200 to directly measure biometric information and an environmental sensor 242 for measuring information (e.g, a temperature) on a surrounding environment. As an example of the EM-based glucose sensor 241, one or more EM-based sensors for measuring various types of biometric information may be included in the external sensor 2(10. The battery 250 may be used to supply power to the external device 200. The X-tal OSC 260 may be used to generate an accurate frequency. The regulator 270 may be used to maintain a constant voltage. The Bluetooth module 280 may be used to communicate with another external device, such as a smartphone. Bluetooth is only an example. Various communication protocols for communicating with another external device and communication modules corresponding to the communication protocols may be used. The AP 220 is a micro control unit (MCU), and may manage the transmission of required power or more (power control) by monitoring power of the implantable device 100 and the external device 200. Furthermore, the AP 220 may control data received from the Bluetooth module 280 and the external sensor 240, and may process data transferred by the implantable device 100. Such management of power or such control/processing of data may be performed according to an algorithm that is included in the AP. The data recovery module 230 may include an in-band data recovery system capable of recovering data transferred by the implantable device 100. For example, the implantable device 100 may modulate measured data into a signal of several hundreds to thousands of kHz through a modulation (LSK, FSK, OSK, etc.) method, and may then transmit the modulated data by carrying the modulated data on a signal of 13.56 MHz. In this case, the data recovery module 230 of the external device 200 may recover a signal for data by demodulating power that shows a normal power level after the power is reduced to a certain degree depending on data and Filtering the signal of 13.56 MHz. In addition, the external device 200 may include a wireless power transmission system for the transfer of power for the driving of the implantable device 100.

Figure 2:
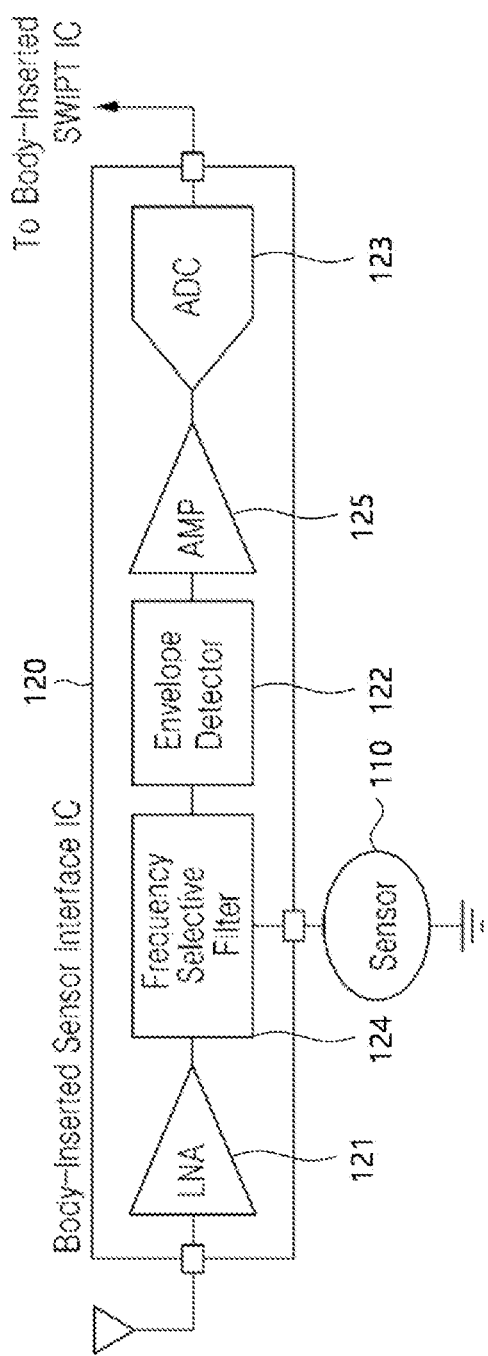
FIG. 2 is a diagram illustrating an example of an internal construction of an implantable device according to an embodiment of the present disclosure.

FIG. 2 is a diagram illustrating an example of an internal construction of the implantable device according to an embodiment of the present disclosure. The sensor interface 120 may measure an S-parameter characteristic of the EM-based sensor 110, that is, a power level of a radio frequency (RE) that is reflected and returned 1w the EM-based sensor 110, and may convert the measured S-parameter characteristic into digital data. The data converted into the digital data may be transmitted to the outside of the body (e.g., the external device 200) by the implantable device 100.

The sensor interface 120 may include the IAA 121 the envelope detector 122, and the ADC 123 as described above. In the embodiment of FIG. 2, the sensor interface 120 may further include a frequency-selective filter 124 and an amplifier (AMP) 125.

The LNA 121 may receive an RF signal that has a specific frequency and that is transmitted by the external device 200. The frequency-selective filter 124 has a frequency-selective characteristic according to a concentration of a target material (e.g., blood glucose) around the EM-based sensor 110 while operating in conjunction with the EM-based sensor 110 inserted into the skin, and may process a filter operation for the size of a signal that is reflected and returned by the EM-based sensor 110. The envelope detector 122 may find the lowest point by converting, into a direct current (DC) level, a signal reflected by S11 among S-parameters. The amplifier 125 may adjust the output of the envelope detector 122 suitably for the ADC 123. The ADC 123 may digitize an amplified signal and transmit the digitized signal to a simultaneous wireless information and power transfer (SWIPT) integrated circuit (IC). Such a SMUT IC may be a circuit including the first circuit that is included in the implantable device 100, among the aforementioned rectifier 130, protector 140, regulator 150, and the resonator 300. The ADC 123 may be implemented to sufficiently handle a signal range of 30 dB or more, for example.

Figure 3:
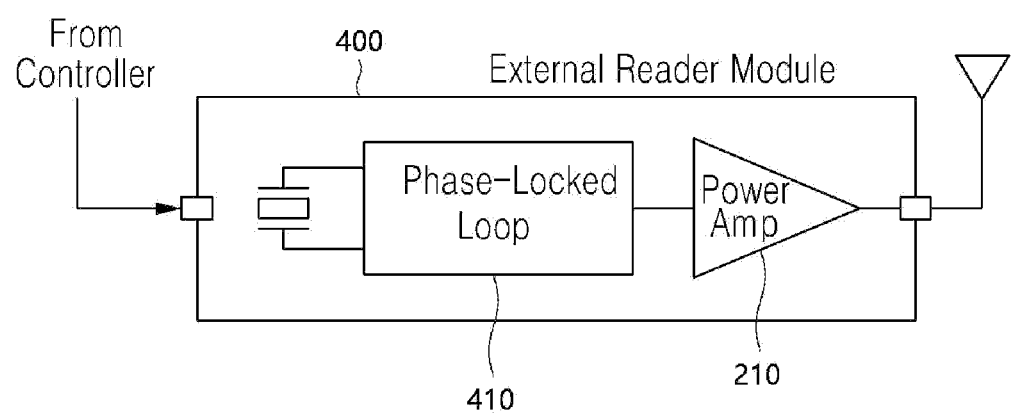
FIG. 3 is a diagram illustrating an example of an internal construction of an external device according to an embodiment of the present disclosure.
Figure 4:
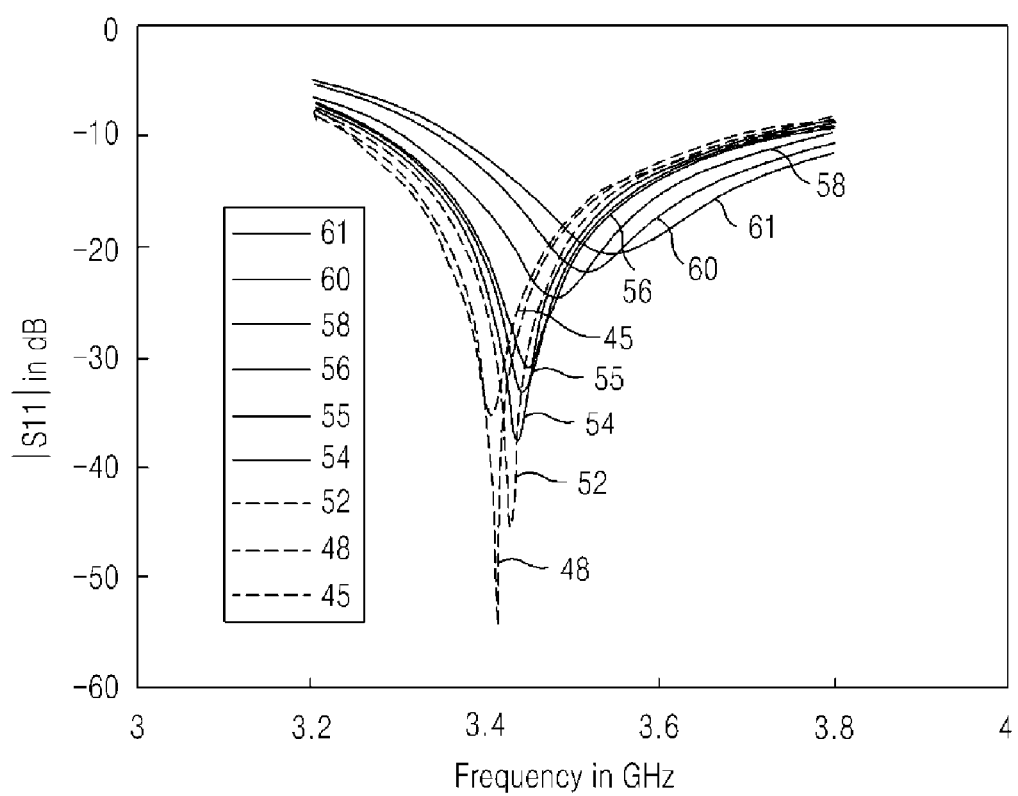
FIG. 4 is a graph illustrating response curves of S11 parameters of the implantable device according to an embodiment of the present disclosure.
Figure 5:
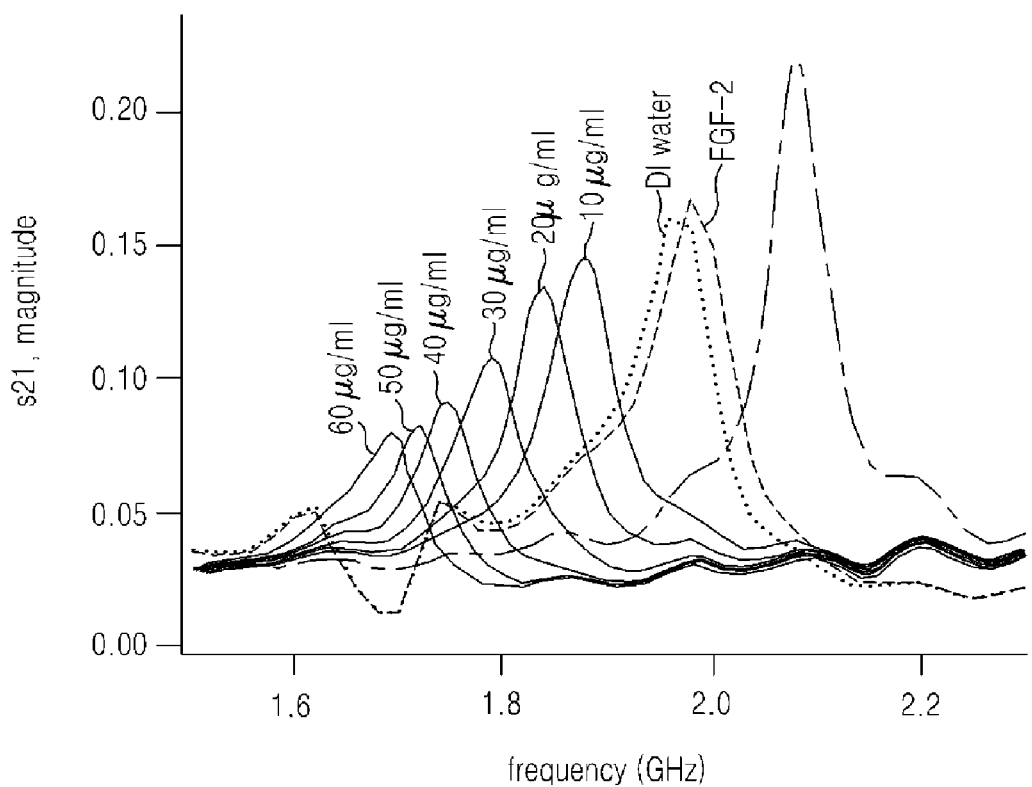
FIG. 5 is a graph illustrating response curves of S21 parameters of the external device according to an embodiment of the present disclosure.

FIG. 3 is a diagram illustrating an example of an internal construction of the external device according to an embodiment of the present disclosure. An external reader module 400 may be included in the external device 200, and may include the power amplifier (AMP) 210 and a phase-locked loop 410. The external reader module 400 may include a frequency sweeping and driving circuit for driving the EM-based sensor 110 over a sufficient wide frequency band so that a change in the S-parameters characteristic of the EM-based sensor 110 included in the implantable device 100 can be measured. Accordingly, the phase-locked loop 410 that constitutes the external reader module 400 may process a frequency scan of the implantable device 100 that is inserted under the skin. The power amplifier 210 may provide power for the driving of the implantable device 100, FIG. 4 is a graph illustrating response curves of S11 parameters of the implantable device according to an embodiment of the present disclosure, and FIG. 5 is a graph illustrating response curves of S21 parameters of the external device according to an embodiment of the present disclosure.

Figure 6:
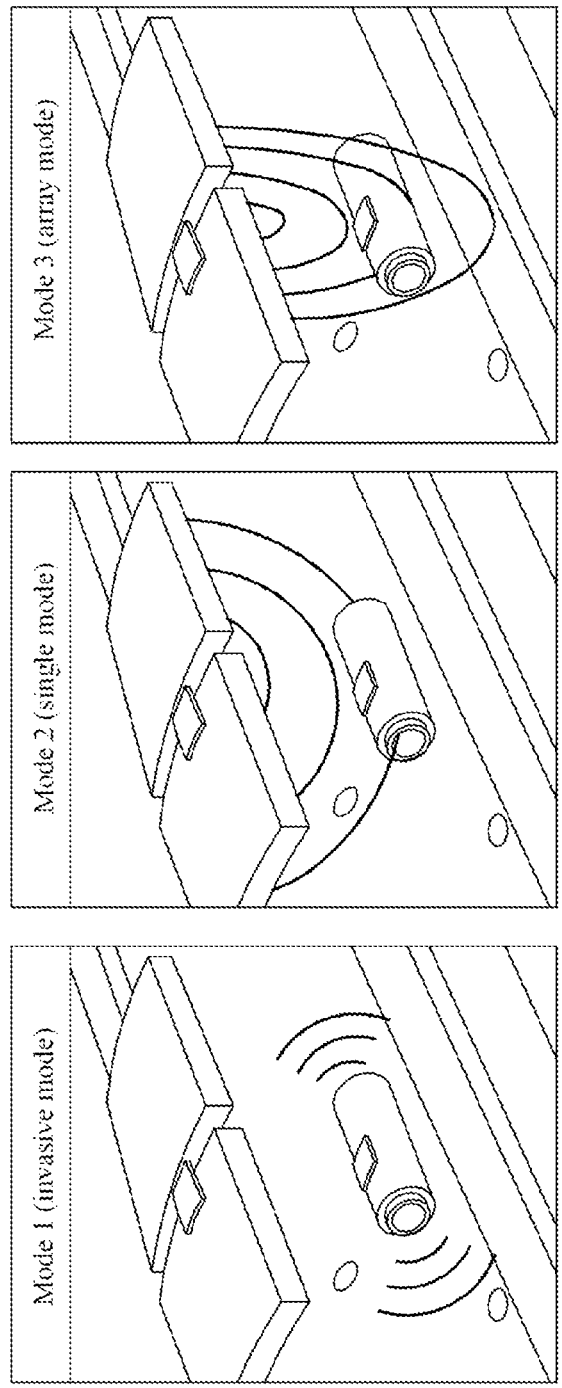
FIG. 6 is a diagram illustrating an operation of a system for measuring biometric information for each mode according to an embodiment of the present disclosure.

FIG. 6 is a diagram illustrating an operation of the system for measuring biometric information for each mode according to an embodiment of the present disclosure. Modes of The system for measuring biometric information may include three modes of an invasive mode, a single mode, and an array mode.

The invasive mode is a mode that plays a role to measure precise blood glucose among the three modes, and may be a mode for measuring a change in blood glucose spread into an interstitial fluid layer at intervals of 5 minutes through an ultra-small-sized EM sensor having a diameter of less than 3 mm, which may be inserted under the skin through a syringe. A sensor for the invasive mode scans electromagnetic waves around the sensor with a dense frequency over a broad band, and may precisely measure a change in permittivity according to a change in blood glucose through characteristic analysis of EM that is reflected for each frequency. Such an invasive mode may enable blood glucose to be accurately measured because influences, such a pressure, a temperature, humidity, and a movement upon measurement, are excluded compared to an EM-based non-invasive external-attachment type blood glucose sensor.

The single mode is a mode which has slightly lower precision than the invasive mode, but is responsible for the measurement of blood glucose in a wider area, and may be a mode for measuring a change in blood glucose in an interstitial fluid layer at intervals of 5 minutes, which is the same as the invasive mode, through an EM sensor that is attached to a surface of an extrasomatic skin. The single mode sensor is a non-invasive blood glucose sensing mode for measuring blood glucose through the analysis of a change in electromagnetic waves that penetrate the interstitial fluid layer based on a change in coupling between two EM sensors. That is, the single mode is slightly coarse, but determines an approximate range of blood glucose over a wide area (coarse scanning). The invasive mode finely scan within a determined range (fine scanning), and may implement heterogeneous sensor redundancy that enables the measurement of an accurate blood glucose value in a wide area that covers 40 to 600 mg/di through the fusions of sensing information of Mode 1 and Mode 2.

The array mode is a mode which has very low precision, but plays a role to detect a danger of a change in blood glucose in real time when the change is great, and may be a mode for monitoring a change in blood glucose within a blood vessel disposed at a deeper place of an interstitial fluid layer in real time through an EM sensor that is attached to a surface of an extrasomatic skin. The array mode sensor may scan a sudden change in blood glucose within a blood vessel in real time based on the principle that the penetration depth of EM is increased by driving several EM sensors simultaneously in parallel. A blood glucose value in the interstitial fluid layer has time delay of about 5 to 20 minutes compared to an actual blood glucose value within a blood vessel. Accordingly, the array mode may implement the real-time measurement of blood glucose based on a change in the blood glucose within the blood vessel.

Figure 7:
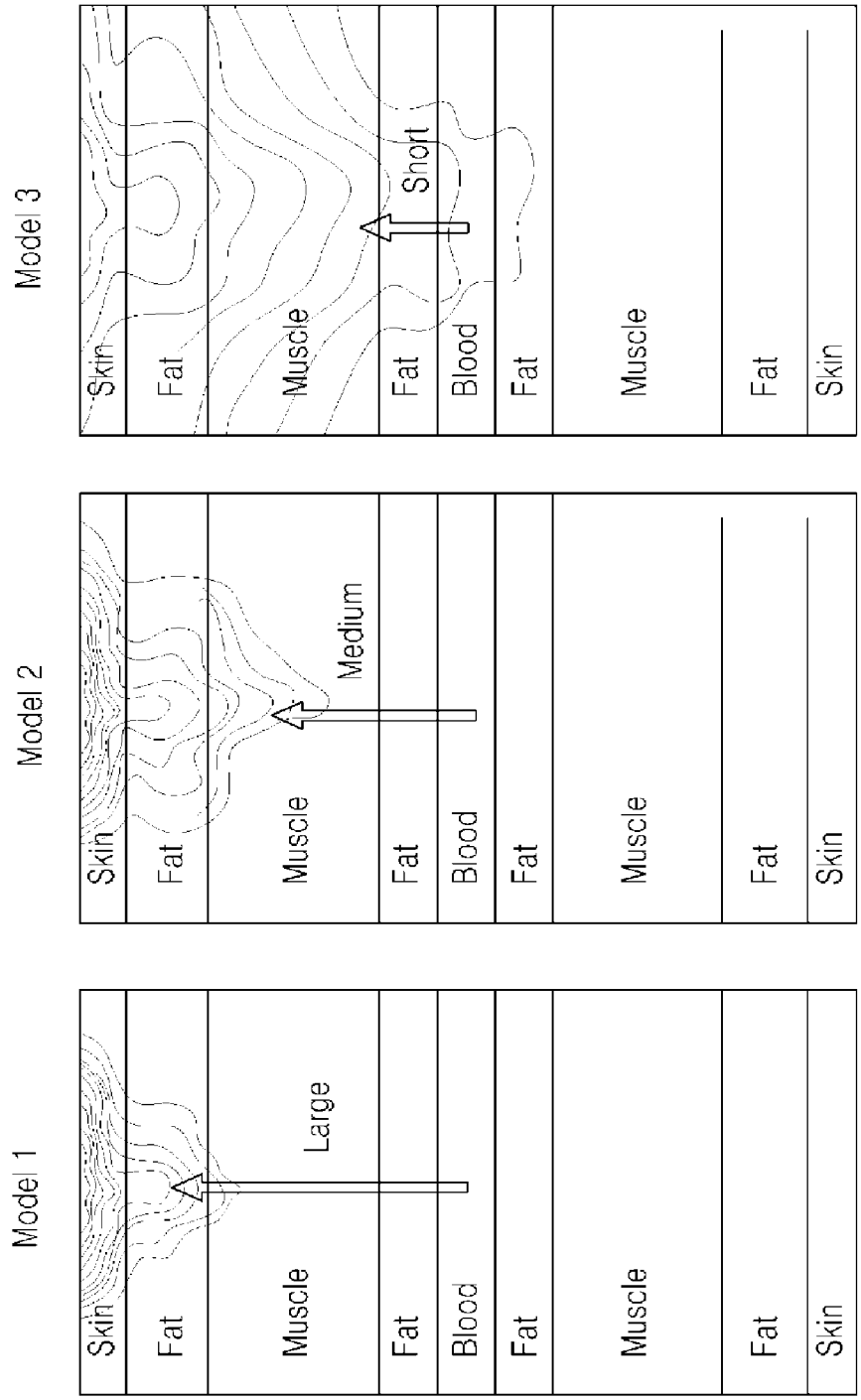
FIG. 7 is a diagram illustrating an electromagnetic wave pattern for each mode, of a blood glucose measurement sensor according to an embodiment of the present disclosure.

FIG. 7 is a diagram illustrating an electromagnetic wave pattern for each mode, of a blood glucose measurement sensor according to an embodiment of the present disclosure. FIG. 7 illustrates examples in which radio waves have reached a subcutaneous layer in the invasive mode, that is, Mode 1, a part of a muscular coat in the single mode, that is, Mode 2, and a blood vessel in the array mode, that is, Mode 3.

Figure 8:
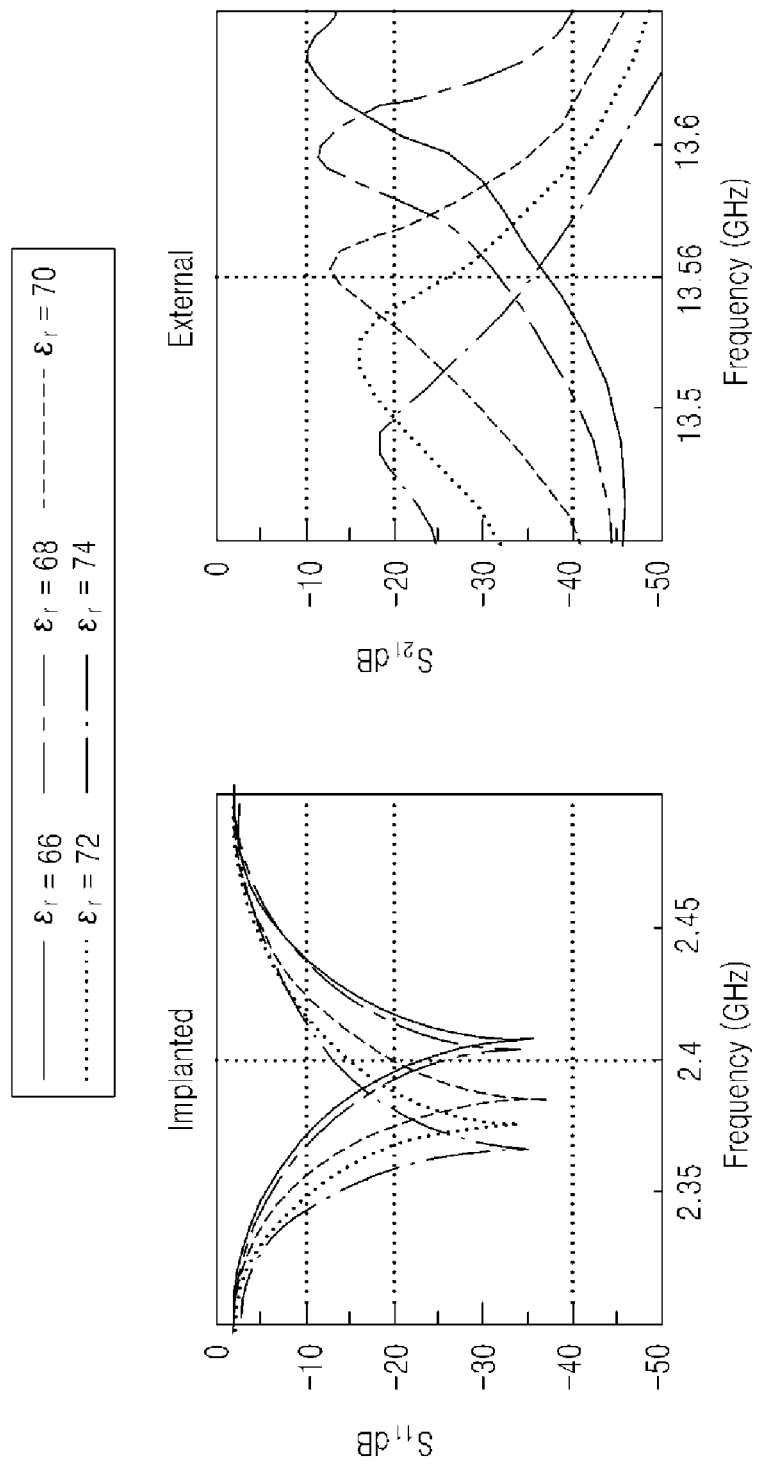
FIG. 8 is graphs illustrating response curves of scattering parameters of the implantable device and the external device in the system for measuring biometric information according to an embodiment of the present disclosure.

FIG. 8 is graphs illustrating response curves of scattering parameters of the implantable device and the external device in the system for measuring biometric information according to an embodiment of the present disclosure. The graphs in FIG. 8 illustrate a change in the resonance frequency in the implantable device 100 and the external device 200 according to a change in biometric information (e,g., blood glucose). A phenomenon in which blood glucose numerical values were lowered when permittivity rose in the implantable device 100 was derived through simulations. When the blood glucose numerical values rise, the permittivity is lowered and the resonance frequency rises.

A frequency generation system for generating a frequency for driving an internal sensor (e.g., the implantable device 100) has a large area. Accordingly, embodiments of the present disclosure, in order to overcome such a problem, the outside (e.g., the external device 200) may transmit a frequency to an internal sensor.

Such a system for measuring biometric information may use a frequency of 13.56 MHz with respect to the transmission of wireless power and data transmission, but the present disclosure is not limited thereto. Power may be supplied from the external device 200 to the implantable device 100 not having a separate power supply unit, such as a battery, through a wireless power transmission scheme, and may be supplied to the sensor interface 120 of the implantable device 100. The external device 200 may generate a sweeping frequency based on a given interval from a frequency of several GHz for driving the implantable device 100 through the external reader module 400, and may transfer the sweeping frequency to the implantable device 100.

The frequency transferred from the external device 200 to the implantable device 100 may drive the EM-based sensor 110. In this case, the permittivity of the EM-based sensor 110 is changed by a change in blood glucose around the EM-based sensor 110, thereby changing the S-parameter characteristic.

A value of the scattering parameter S11 is lowered in a specific resonance frequency. In order to find the lowest point, the external device 200 sweeps a frequency over a wide band through the external reader module 400, and transfer the swept frequency to the implantable device 100. In each of frequency characteristics reflected by the EM-based sensor 110, a frequency-selective characteristic may be changed and filtered by the frequency-selective filter 124 based on a concentration of a large material (e.g., blood glucose) nearby as in the EM-based sensor 110. Each of the frequencies may be transferred to the envelope detector 122. The envelope detector 122 may find a minimum value. If the size of an output in the envelope detector is too large or small, this may affect the input of the ADC 123. Accordingly, the size of a signal input to the ADC 123 may be adjusted as an input of 30 dB or more through a baseband amplifier (e.g., the amplifier 125). An output adjusted by the baseband amplifier may be input as an input to the ADC 123, may be converted into digital data of 0 and 1, and may be transferred to the external device 200 through a back scattering communication scheme, such as load shift keying (LSK) modulation. The external device 200 may generate data for biometric information by using the digital data transferred by the implantable device 100, and may transfer the generated data to another external device (e.g., a smartphone) through the communication module.

Figure 9:
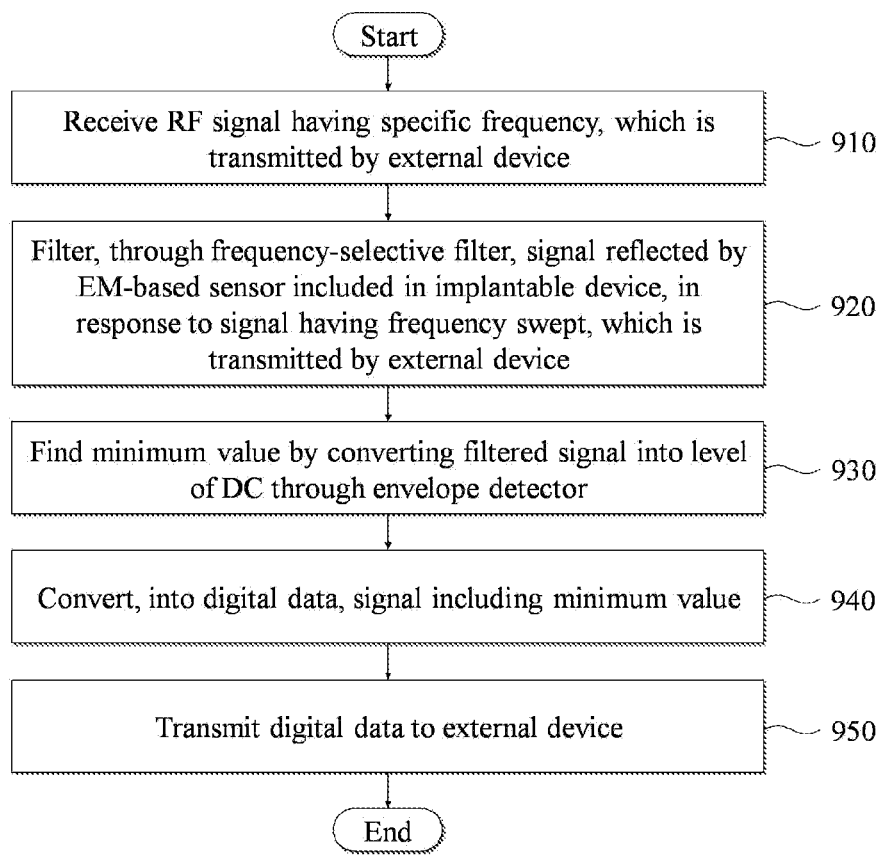
FIG. 9 is a diagram illustrating an example of a method of measuring, by the implantable device, biometric information according to an embodiment of the present disclosure.

FIG. 9 is a diagram illustrating an example of a method of measuring, by the implantable device, biometric information according to an embodiment of the present disclosure. The method of measuring biometric information according to the present embodiment may be performed by the aforementioned implantable device 100.

In step 910, the implantable device 100 may receive an RF signal having a specific frequency, which is transmitted by the external device 200. In this case, the received RF signal may include power that is transmitted through wireless power transmission, and may be used for the driving of the implantable device 100.

In step 920, the implantable device 100 may filter, through the frequency-selective filter 124, a signal reflected by the EM-based sensor 110 included in the implantable device, in response to a signal having a frequency swept, which is transmitted by the external device 200. Blood glucose may be measured based on a characteristic in which a resonance frequency is changed in response to permittivity around the implantable device 100. To this end, the external device 200 may transfer a signal to the implantable device 100 while sweeping the frequency through the phase-locked loop 410. In this case, the implantable device 100 may receive the signal reflected by the EM-based sensor 110, may filter the received signal through the frequency-selective filter 124, and may output signals having the filtered frequency.

In step 930, the implantable device 100 may find a minimum value by converting the filtered signal into a DC level through the envelope detector 122.

In step 940, the implantable device 100 may convert, into digital data, the signal including the minimum value. For example, the implantable device 100 may amplify the size of the signal having the minimum value to a given size or more through the amplifier 125, and may convert the amplified signal into the digital data through the ADC 123.

Figure 10:
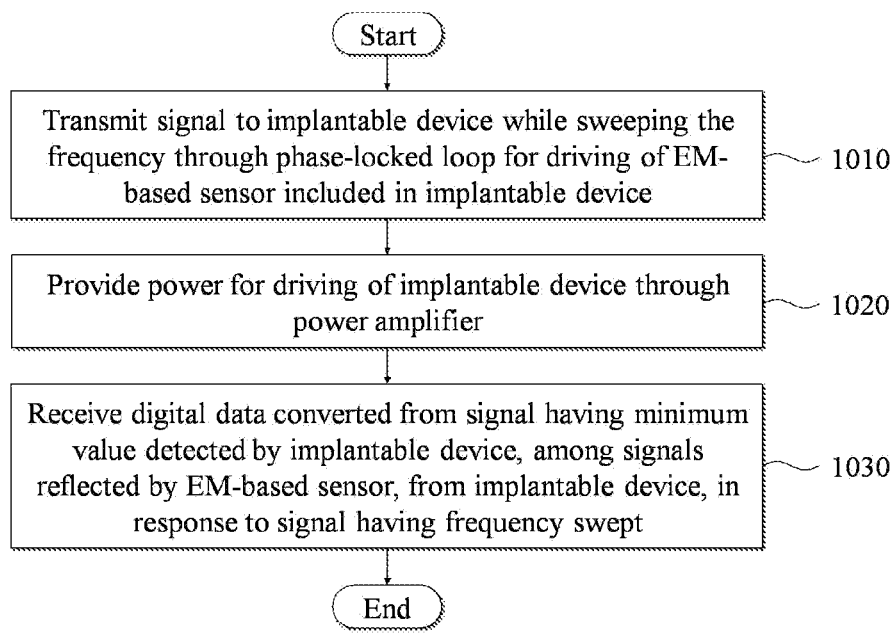
FIG. 10 is a diagram illustrating an example of a method of measuring, by the external device, biometric information according to an embodiment of the present disclosure.

In step 950, the implantable device 100 may transmit the digital data to the external device 200. As described above, the digital data may be transferred to the external device 200 through the SWIFT IC, FIG. 10 is a diagram illustrating an example of a method of measuring, by the external device, biometric information according to an embodiment of the present disclosure. The method of measuring biometric information according to the present embodiment may be performed by the aforementioned external device 200.

In step 1010, for the driving of the EM-based sensor 110 included in the implantable device 100, the external device 200 may transmit a signal to the implantable device 100 while sweeping the frequency through the phase-locked loop 410.

In step 1020, the external device 200 may provide power for the driving of the implantable device 100 through the power amplifier. For example, the external device 200 may transmit an RF signal having a specific frequency to the implantable device 100 through the power amplifier 210.

In step 1030, the external device 200 may receive digital data converted from a signal having a minimum value detected by the implantable device 100, among signals reflected by the EM-based sensor 110, from the implantable device, in response to a signal having a frequency swept. In this case, the external device 200 may measure blood glucose based on a characteristic in which a resonance frequency is changed based on permittivity around the implantable device.

FIGS. 11 to 14 are diagrams illustrating examples of a magnetic dipole moment. A material having an N pole on one side thereof and an S pole on the other side thereof like a magnet is called a magnetic dipole. In an electric force, units that generate an electric force are (−) charges and (+) charges. A material may be classified as a material electrically having a (−) pole or a (+) pole, and may have an electric force phenomenon that acts between the (−) pole and the (+) pole. However, the material having the magnetic force cannot be divided into the N pole and the S pole, and has a magnetic dipole form always having the N pole on one side thereof and the S pole on the other side thereof. In this case, the size of the magnetic dipole may be indicated as a magnetic dipole moment. For example, when a current I flows into a circular electric wire, if the width of the circular electric wire is 5, the size of the magnetic dipole moment is a value IS obtained by multiplying the current and the width. The direction of the magnetic dipole moment is a direction indicated by the thumb when a right index finger is surrounded in the direction of the current.

Figure 11:
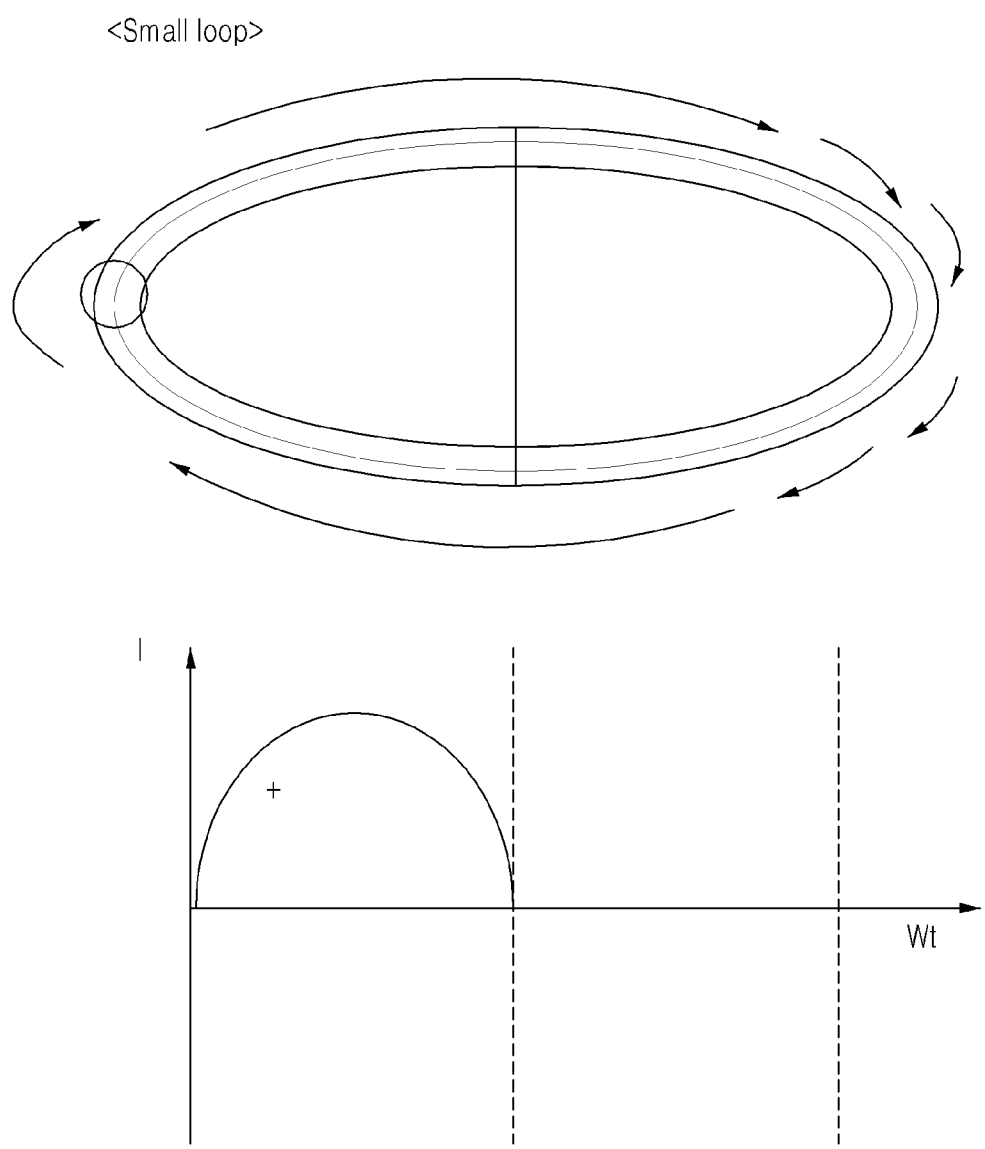
FIGS. 11 to 14 are diagrams illustrating examples of a magnetic dipole moment.
Figure 12:
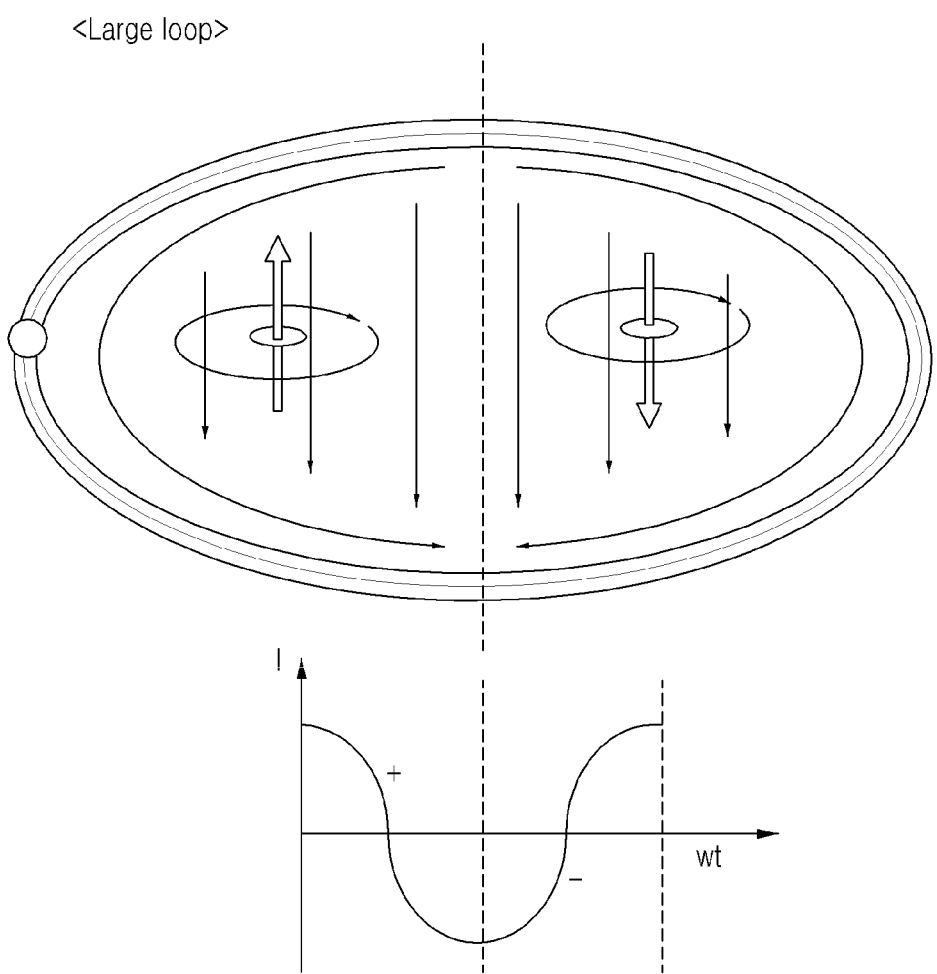
Figure 13:
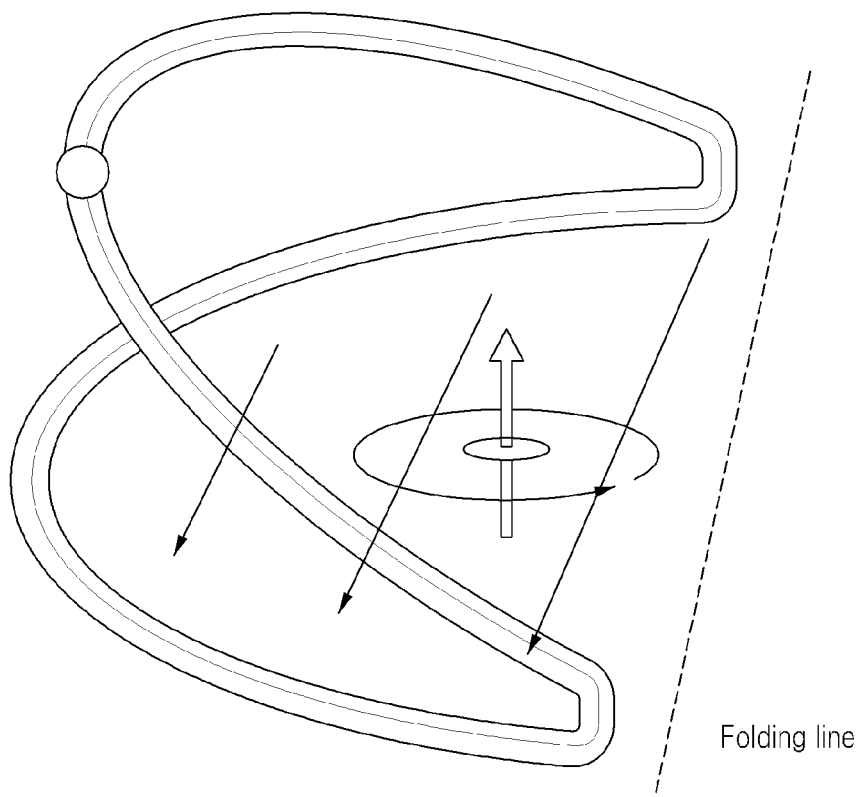
Figure 14:
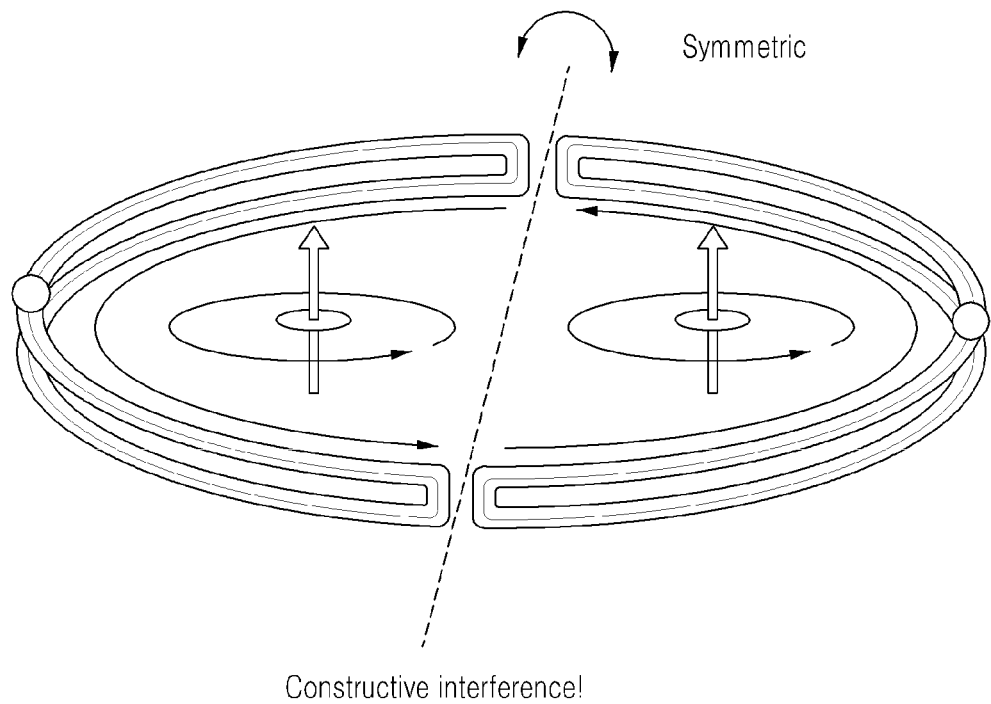

In this case, FIG. 11 is an example of a small loop. The small loop has a circumference of λ/2, and is rotated in one direction, but may have magnetic dipole moment resonance asymmetrically to a current. FIG. 12 is an example of a large loop. The large loop has a circumference of X., and has currents in opposite directions, so that magnetic dipole moments may be offset. FIGS. 13 and 14 are examples (a, folded single loop in FIG. 13 and a folded double loop in FIG. 14) of folded loops, and illustrate that a strong magnetic dipole moment is generated and constructive interference may be generated when the loop having a circumference of 2, is folded.

If a shape (e.g., the small loop in FIG. 11) having a half wavelength circumference (a circumference of λ/2) of the most common loop is applied for magnetic dipole resonance, the shape is rotated in one direction, but a magnetic dipole moment may have valid resonance due to the asymmetry of currents. In this case, in the case of a circumference having one wavelength (a circumference of: λ), magnetic dipole moments may be offset because currents have opposite directions. However, if the loop is folded, a current in the same direction is formed (the folded single loop in FIG. 13). If an in-phase loop is disposed on the other side (the folded double loop in FIG. 14), a strong magnetic dipole moment may be generated.

Figure 15:
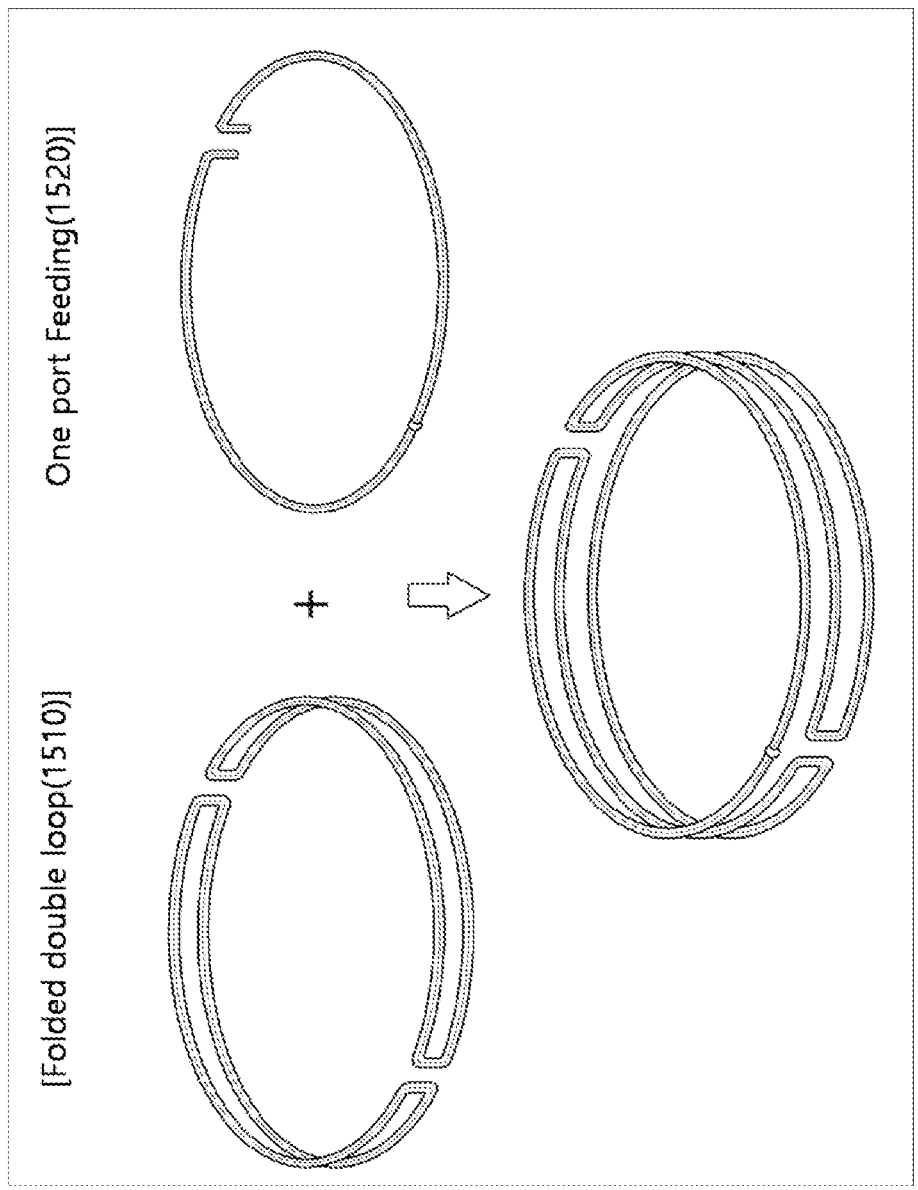
FIGS. 15 and 16 are diagrams illustrating examples of a folded loop having a single feeding structure in an embodiment of the present disclosure.
Figure 16:
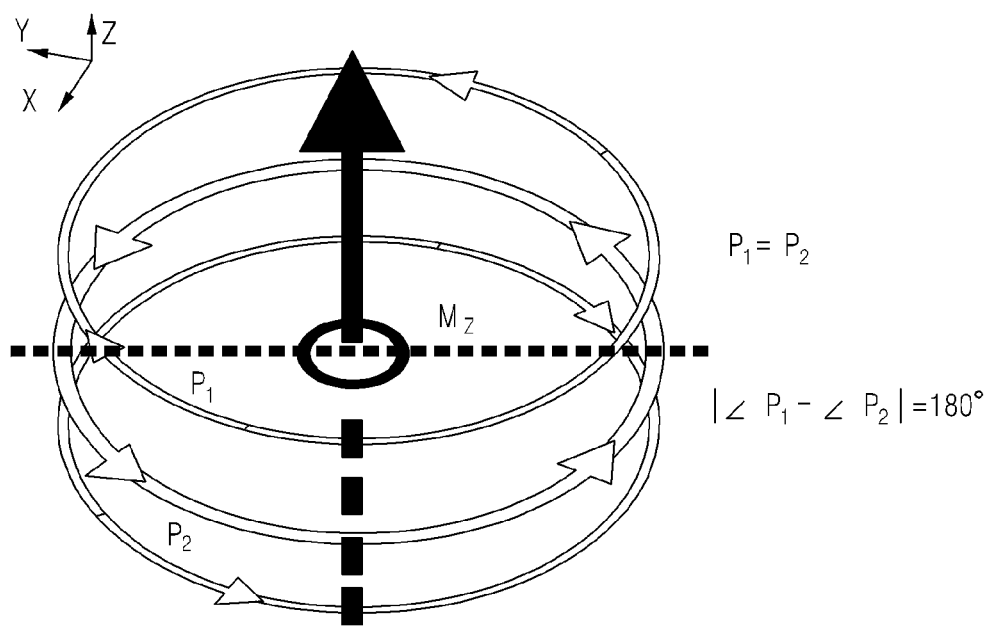

FIGS. 15 and 16 are diagrams illustrating examples of a folded loop having a single feeding structure in an embodiment of the present disclosure. The folded loop according to the present embodiment may be an example of an implantable sensor included in the implantable device 100. A shape of such an implantable sensor may enable magnetic dipole resonance through single feeding by merging one port feeding 1520 and a folded double loop 1510. FIG. 15 illustrates a shape in which a first side of the one port feeding 1520 is connected to a first side at the top of a first folded loop of the folded double loop 1510, a second side of the one port feeding 1520 is connected to a first side at the top of a second folded loop of the folded double loop 1510, and a second side at the bottom of the first folded loop and a second side at the bottom of the second folded loop are connected. In this case, although not illustrated in FIG. 15, the one port feeding 1520 may also be connected to a power source, and a current may be applied to the triple folded loop structure.

Such a triple folded loop structure is a vertical symmetry shape and may form sub-radiative resonance by inducing the offset of currents.

Figure 17:
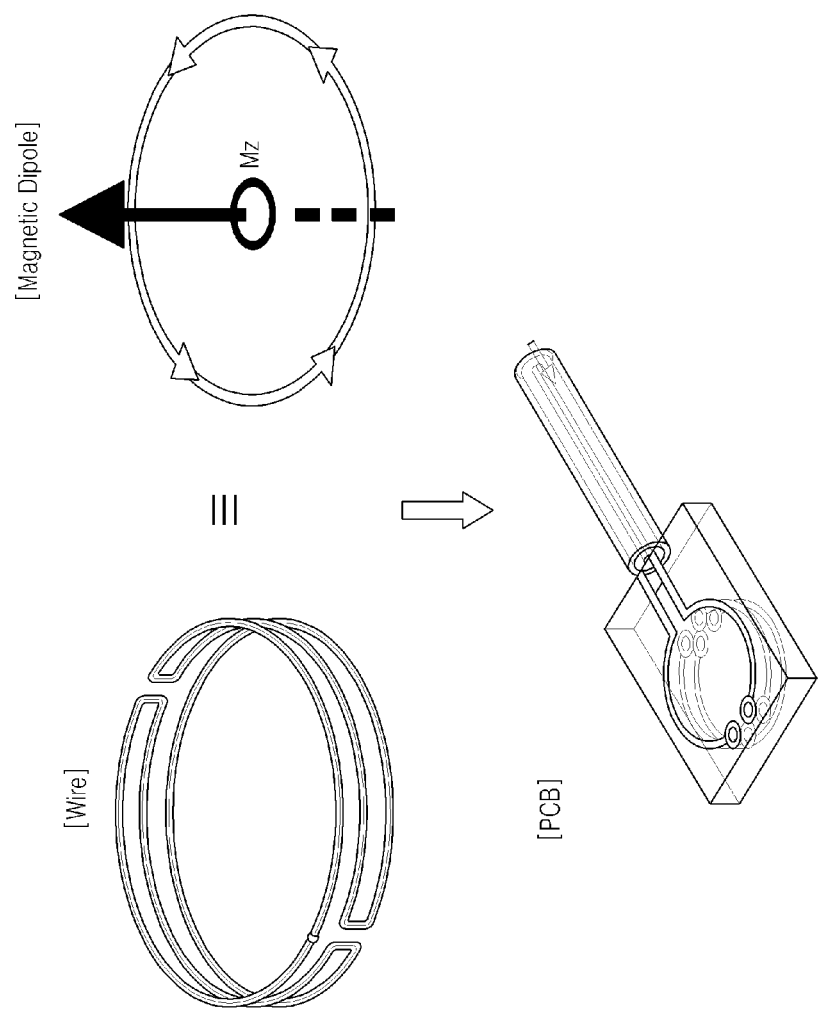
FIG. 17 is a diagram illustrating an example of the principle and design process of an insertion type sensor in an embodiment of the present disclosure.
Figure 18:
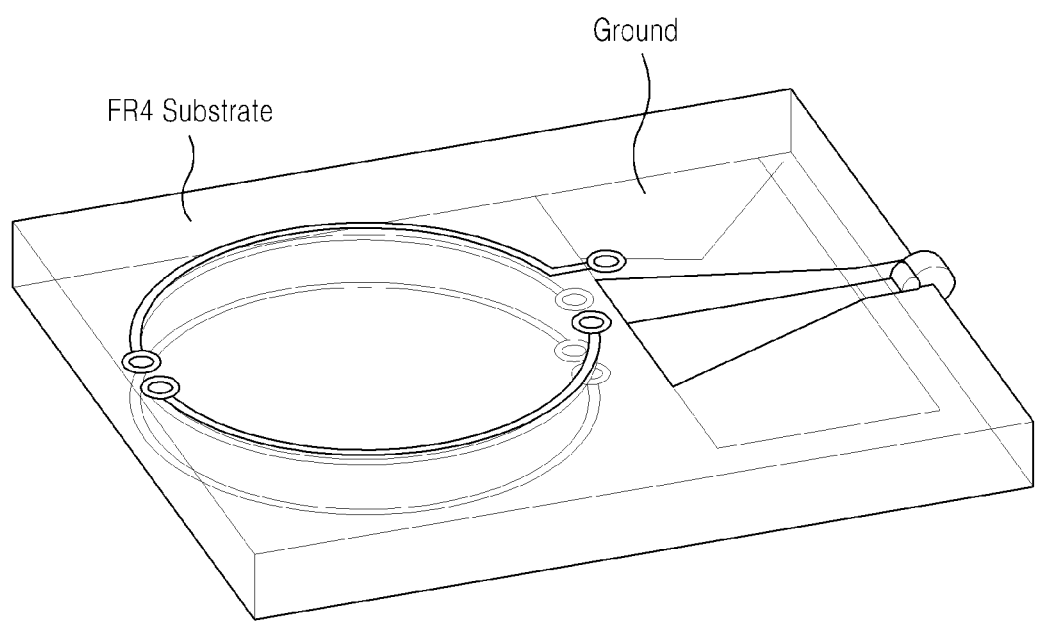
FIG. 18 is a diagram illustrating an example of a printed circuit board (PCB) in which a triple loop structure has been implemented in an embodiment of the present disclosure.
Figure 19:
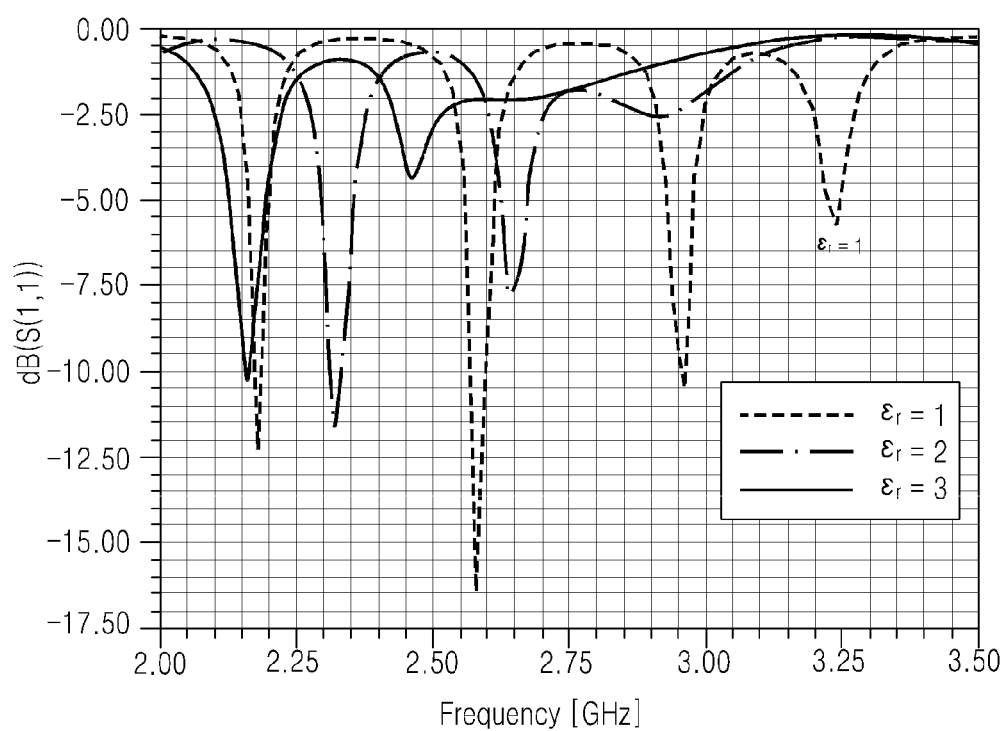
FIG. 19 is a graph illustrating an example of a change in resonance of a sensor according to permittivity in an embodiment of the present disclosure.

FIG. 17 is a diagram illustrating an example of the principle and design process of an implantable sensor in an embodiment of the present disclosure. FIG. 18 is a diagram illustrating an example of a printed circuit board (PCB) in which a triple loop structure has been implemented in an embodiment of the present disclosure, FIG. 19 is a graph illustrating an example of a change in resonance of a sensor according to permittivity in an embodiment of the present disclosure.

In this case, FIG. 17 illustrates a vertical symmetry shape and that a magnetic dipole moment may be formed in one direction and sub-radiative resonance may be formed by inducing the offset of current by the triple loop structure, FIG. 18 illustrates an example in which such a triple loop structure has been implemented in the PCB of an FR4 substrate. From FIG. 19, it may be seen that a resonance point is changed because permittivity is changed.

Figure 20:
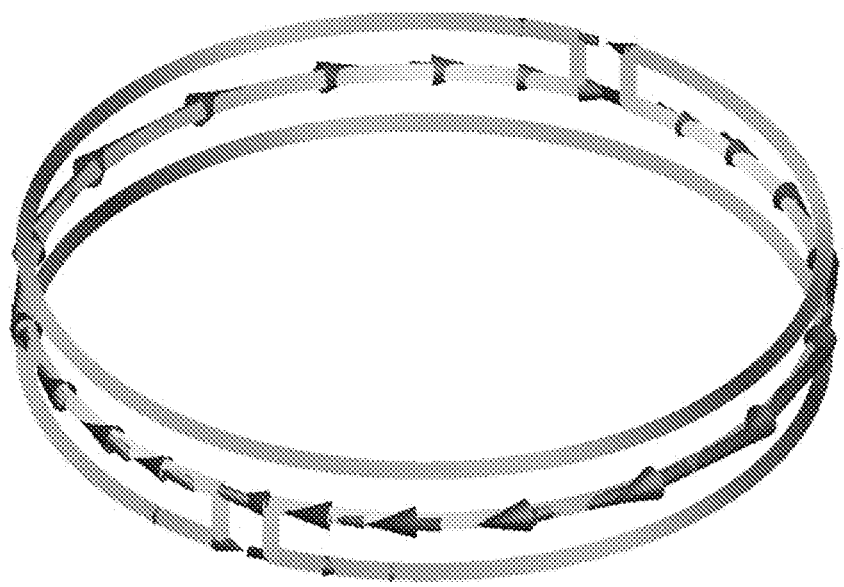
FIG. 20 is a diagram illustrating an example of a current that flows into the insertion type sensor structure in an embodiment of the present disclosure.
Figure 21:
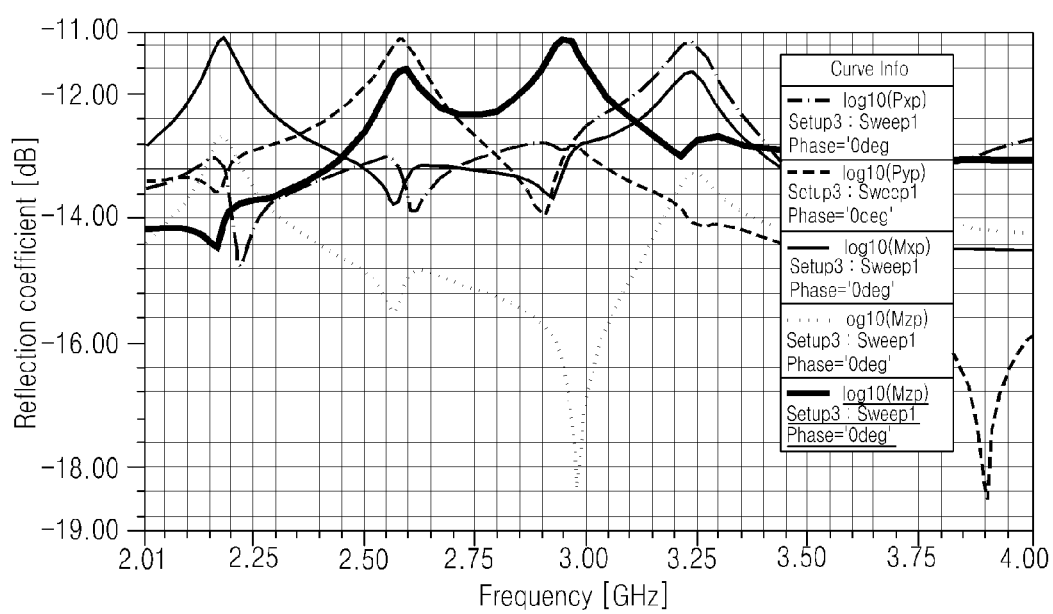
FIG. 21 is a graph illustrating an example of the results of multi-pole expansion of the insertion type sensor in an embodiment of the present disclosure.
Figure 22:
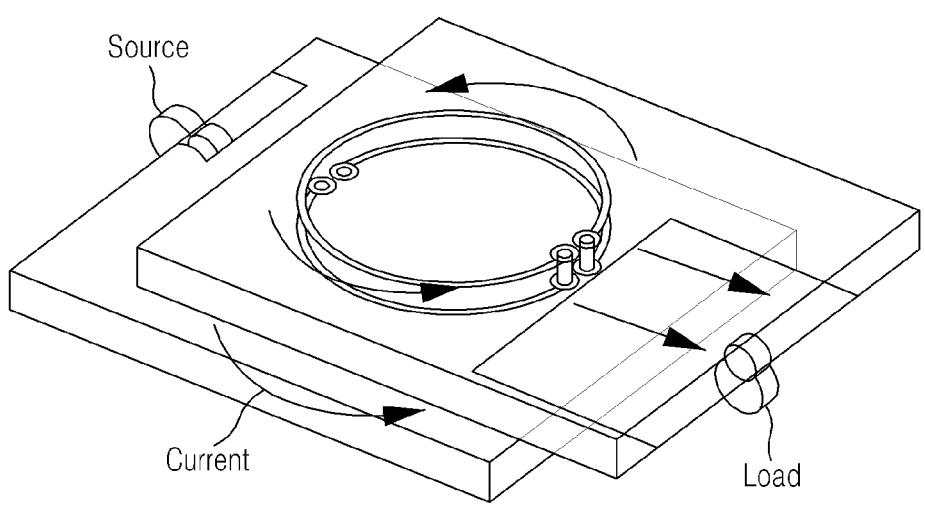
FIG. 22 is a diagram illustrating that a reader on the upper side can read out a current flowing into the insertion type sensor structure by using magnetic coupling in an embodiment of the present disclosure.

FIG. 20 is a diagram illustrating an example of a current that flows into the implantable sensor structure in an embodiment of the present disclosure. FIG. 21 is a graph illustrating an example of the results of multi-pole expansion of the implantable sensor in an embodiment of the present disclosure. FIG. 22 is a diagram illustrating that an external sensor (e.g., a sensor of the external device 200) on the upper side thereof may read out a current that flows into an implantable sensor (e.g., a sensor of the implantable device 100) structure by using magnetic coupling in an embodiment of the present disclosure.

In this case, FIG. 20 illustrates how a current flows into the loop structure of the implantable sensor in a 2.9 GHz band. FIG. 21 illustrates the results of multi-pole expansion according to the flow of the current. As in a red line in the graph of FIG. 21, it can be seen that a magnetic dipole is maximized in the 2.9 GI-Iz band in which resonance is generated. Based on such a phenomenon, by using magnetic coupling as in FIG. 22, a current that flows into the implantable sensor on the lower side thereof may be induced into an external sensor on the upper side of the implantable sensor. Accordingly, a signal may be read out through the external sensor.

Figure 23:
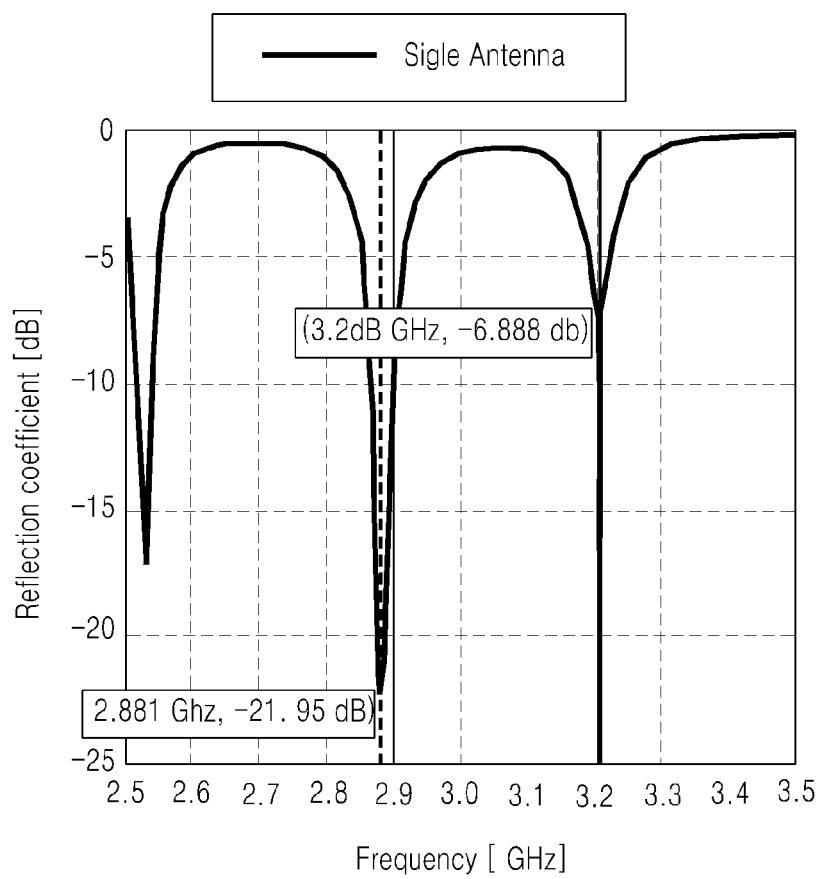
FIG. 23 is a graph illustrating an example of the results of measurement of an S11 parameter by a single sensor in an embodiment of the present disclosure.
Figure 24:
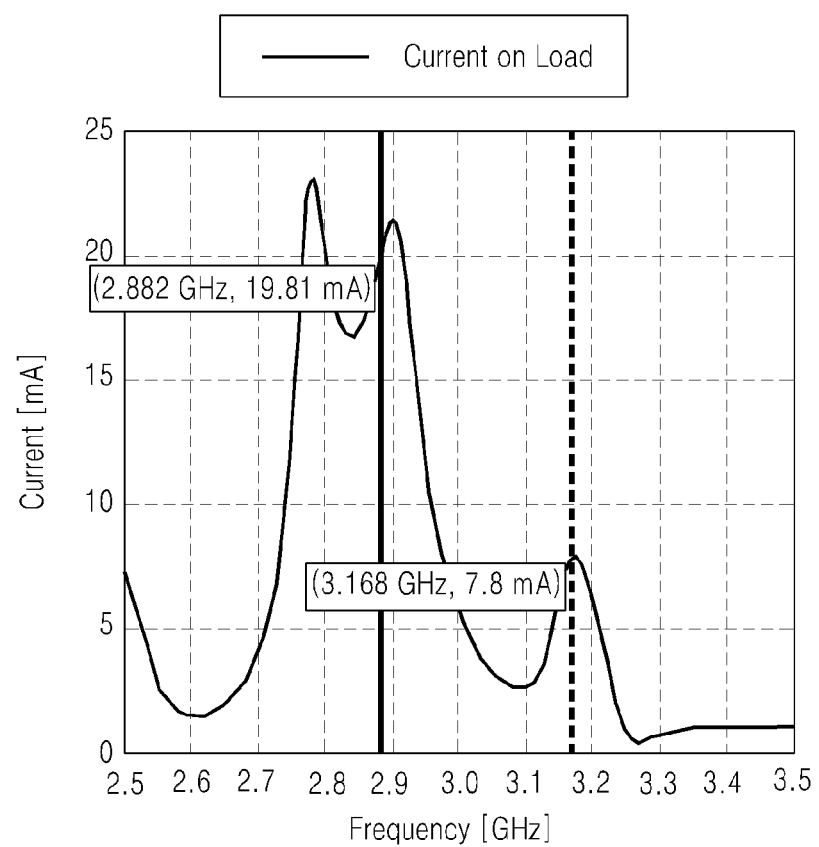
FIG. 24 is a graph illustrating an example of a current applied to a load of the reader in an embodiment of the present disclosure.

FIG. 23 is a graph illustrating an example of the results of measurement of an Sit parameter by a single sensor in an embodiment of the present disclosure. FIG. 24 is a graph illustrating an example of a current applied to a load of the reader in an embodiment of the present disclosure. As in FIG. 22, after an external sensor is disposed in parallel to an implantable sensor on the upper side thereof, feeding is connected to the implantable sensor, and a load is applied to the external sensor, a magnetic dipole becomes dominant through a current loop that is generated in the implantable sensor. A current is induced into the loop structure of the external sensor through an eddy current according to the magnetic dipole. The graph of FIG. 24 is a graph illustrating a current applied to the load of the external sensor. It may be seen that a current has been induced in the current loop of the external sensor. In other words, the implantable sensor may measure S-parameters as in the graph of FIG. 23, and may transfer the S-parameters to the external sensor.

Figure 25:
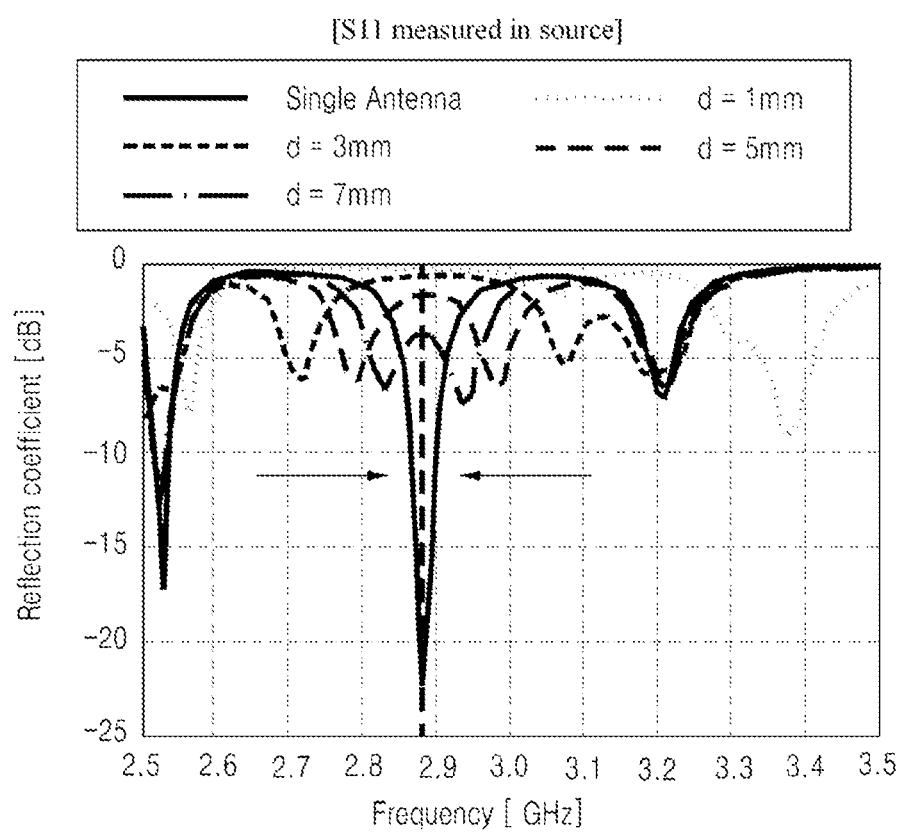
FIGS. 25 and 26 are graphs illustrating examples of a change in the frequency characteristic according to the distance between the implantable sensor and the external sensor in an embodiment of the present disclosure.
Figure 26:
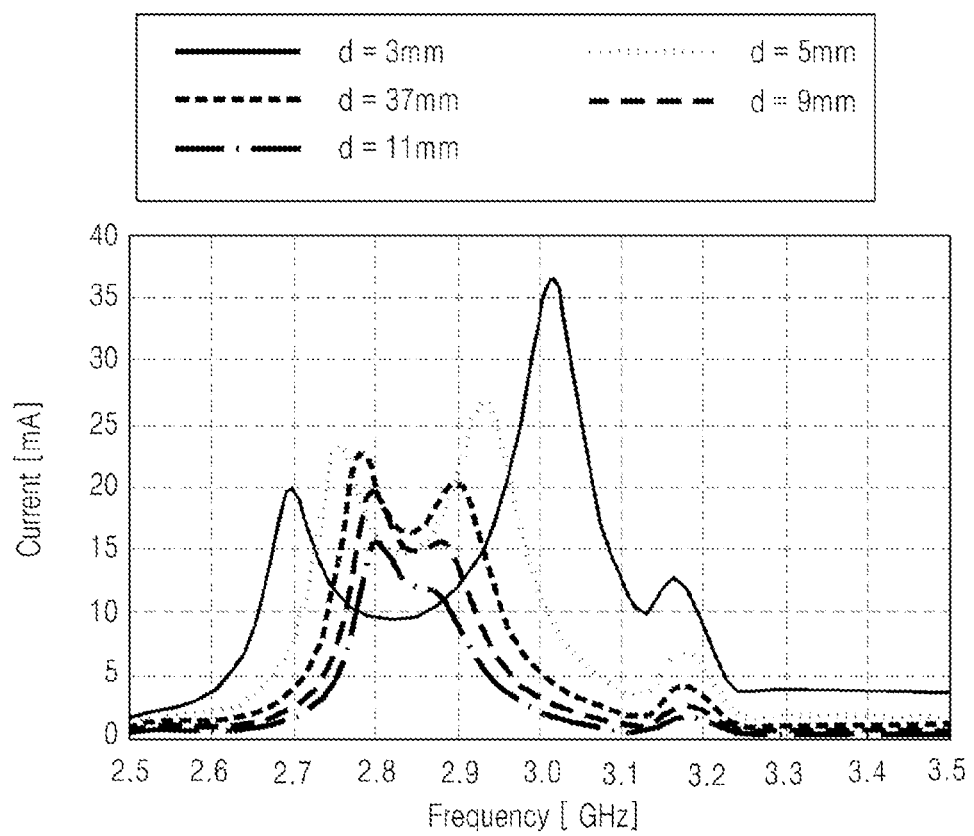

FIGS. 25 and 26 are graphs illustrating examples of a change in the frequency characteristic according to the distance between the implantable sensor and the external sensor in an embodiment of the present disclosure.

After a middle part of the loop of the implantable sensor and the loop of the external sensor was disposed on one axis and the loops were disposed in parallel, S-parameters according to a frequency were analyzed through simulations while changing a distance d between the implantable sensor and the external sensor. The graph of FIG. 25 illustrates that as the distance d between the implantable sensor and the external sensor is reduced, reflection in a resonant part, which is generated by a magnetic dipole in a single sensor (the implantable sensor), is increased. The graph of FIG. 26 illustrates that as the distance d is reduced, two current peaks of a current applied to a load become distant from each other on the basis of a frequency in which a magnetic dipole is generated. In contrast, it may be easily understood that the distance between, the implantable sensor and the external sensor can be measured based on such as a change in the frequency characteristic.

Figure 27:
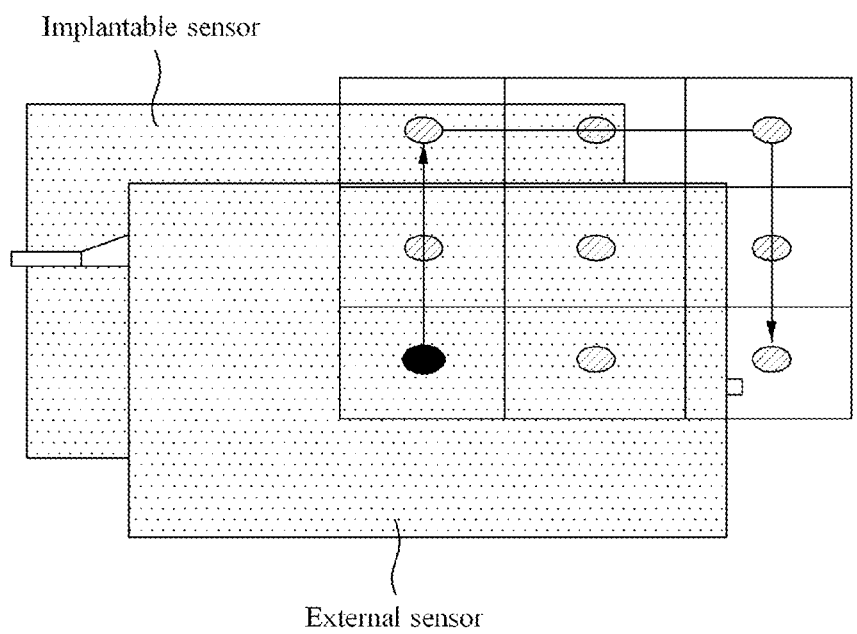
FIG. 27 is a diagram illustrating an example of a movement of the location of the external sensor in an embodiment of the present disclosure.
Figure 28:
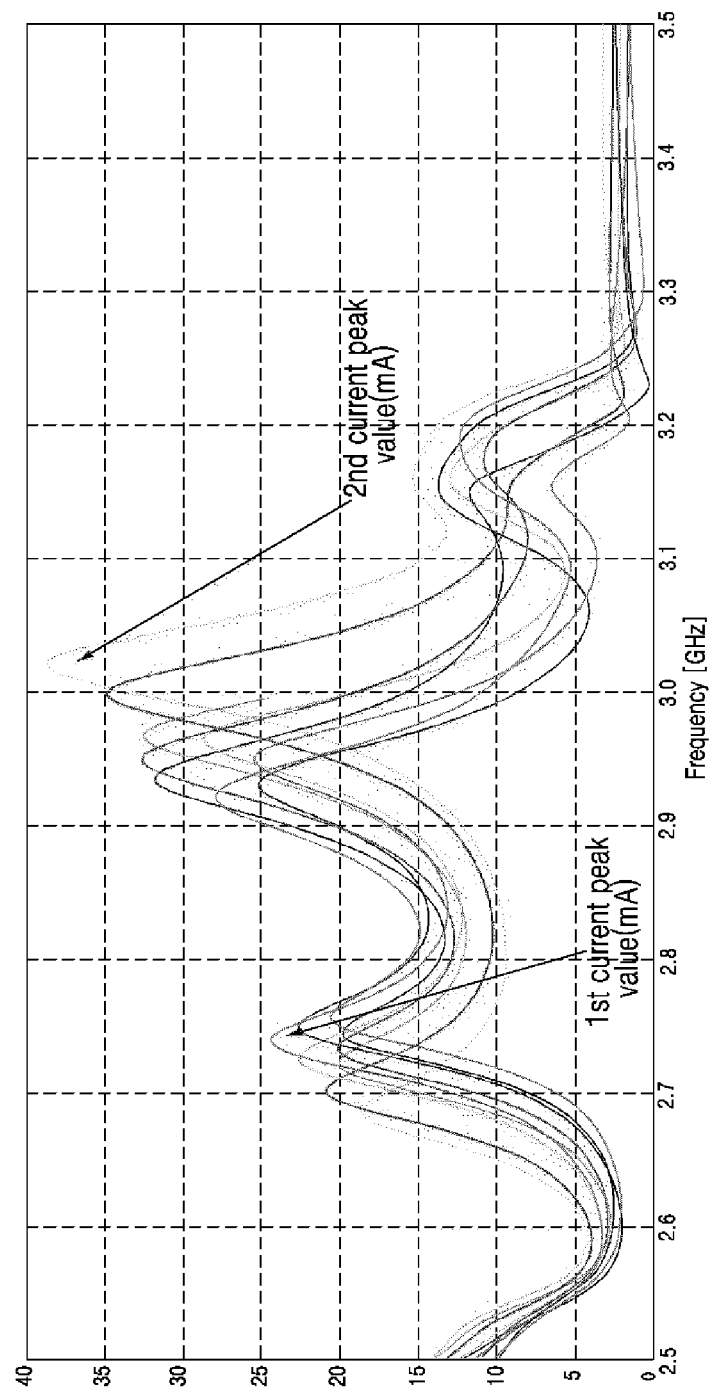
FIG. 28 is a graph illustrating the measurement of a current applied to a load of the external sensor in an embodiment of the present disclosure.
Figure 29:
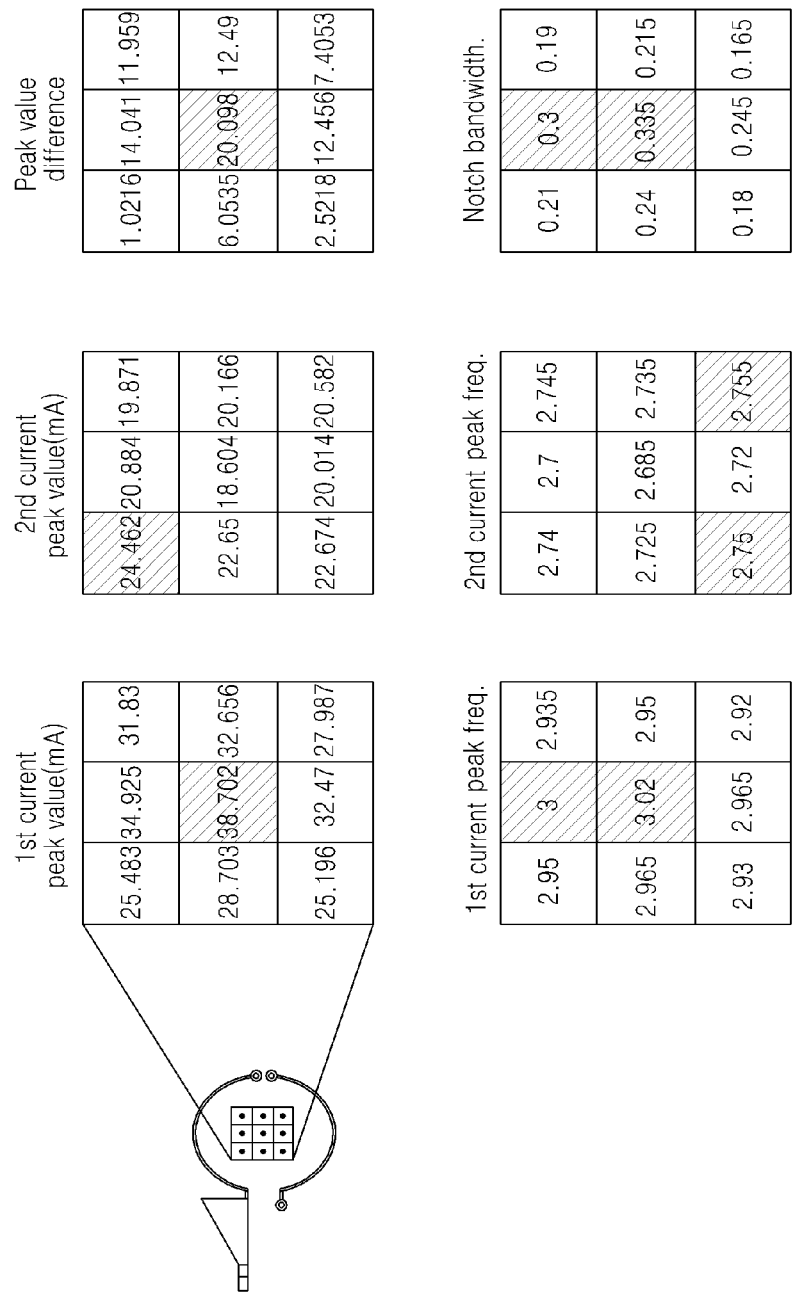
FIG. 29 is a diagram illustrating an example of data in which values, such as a maximum value, a minimum value, and a notch bandwidth in the graph of the current applied to the load of the external sensor have been visualized with colors in an embodiment of the present disclosure.

FIG. 27 is a diagram illustrating an example of a movement of the location of an external sensor in an embodiment of the present disclosure. FIG. 28 is a graph illustrating the measurement of a current applied to a load of an external sensor in an embodiment of the present disclosure. FIG. 29 is a diagram illustrating an example of data illustrating values, such as a maximum value, a minimum value, and a notch bandwidth in the graph of the current applied to the load of the external sensor in an embodiment of the present disclosure. It may be seen that when middle alignment becomes a straight line, a current applied to a load of the external sensor has one of [a maximum value] and [the minimum value], which may be applied to an actual product. In other words, if a middle part of the loop of the implantable sensor and the loop of the external sensor is placed on one axis, the current applied to the load of the external sensor may have a maximum value. This may mean that the implantable sensor may operate as an alignment key. When the implantable sensor may operate as the alignment key, this may mean that the location of the implantable sensor of the implantable device 100 within the body can be accurately measured by the external device 200 through the external sensor outside the body.

Meanwhile, in the aforementioned embodiments, examples in which the loops of the Implantable sensor and the external sensor are circles are described. However, according to an embodiment, the loops of the implantable sensor and the external sensor may be implemented in an oval shape, in this case, the external device 200 may detect even a direction of the implantable sensor based on a magnetic field (e.g., the aforementioned fringing field) that is formed by the loop having an oval shape. For example, in loops having two ovals which are disposed on the upper and lower sides thereof, a current applied to the load of the external sensor when the long axes of the two ovals are parallel to each other may have a maximum value. As the long axes of the two ovals are twisted with respect to each other (as an angle between the long axes is increased), the current applied to the load of the external sensor may be reduced. Accordingly, even a current direction of the implantable sensor can be checked through the intensity of such a current.

The location, distance, and direction of the implantable sensor may be extended and recognized as the location, distance, and direction of the implantable device 100 including the implantable sensor.

In this case, according to embodiments of the present disclosure, blood glucose can be accurately measured by measuring a characteristic change attributable to a change in the blood glucose through the implantable device and the external device. Furthermore, the location of the implantable device within the body can be accurately checked by the external device outside the body.

j The aforementioned device may be implemented as a hardware component or a, combination of a hardware component and a software component. For example, the device and component described in the embodiments may be implemented using one or more general-purpose computers or special-purpose computers, such as a processor, a controller, an arithmetic logic unit (ALU), a digital signal processor, a microcomputer, a field programmable gate array (FPGA), a programmable logic unit (PLU), microprocessor, or any other device capable of executing or responding to an instruction, The processing device may perform an operating system (OS) and one or more software applications that are executed on the OS. Furthermore, the processing device may access, store, manipulate, process, and generate data in response to the execution of software. For convenience of understanding, one processing device has been illustrated as being used, but a person having ordinary knowledge in the art may understand that the processing device may include a plurality of processing elements and/or a plurality of types of processing elements. For example, the processing device may include a plurality of processors or one processor and one controller. Furthermore, another processing configuration, such as a parallel processor, is also possible.

Software may include a computer program, a code, an instruction or a combination of one or more of them, and may configure a processing device so that the processing device operates as desired or may instruct the processing devices independently or collectively. The software and/or the data may be embodied in any type of machine, a component, a physical device, or a computer storage medium or device in order to be interpreted by the processing device or to provide an instruction or data to the processing device. The software may be distributed to computer systems that are connected over a network, and may be stored or executed in a distributed manner. The software and the data may be stored in one or more computer-readable recording media.

The method according to an embodiment may be implemented in the form of a program instruction executable by various computer means, and may be stored in a computer-readable medium. The medium may continue to store a program executable by a computer or may temporarily store the program for execution or download. Furthermore, the medium may be various recording means or storage means having a form in which one or a plurality of pieces of hardware has been combined. The medium is not limited to a, medium directly connected to a computer system, but may be one distributed over a network. An example of the medium may be one configured to store program instructions, including magnetic media such as a hard disk, a floppy disk and a magnetic tape, optical media such as CD-ROM and a DVD, magneto-optical media such as a floptical disk, ROM, RAM, and a flash memory. Furthermore, other examples of the medium may include an app store in which apps are distributed, a site in which other various pieces of software are supplied or distributed, and recording media and/or storage media managed in a server.

As described above, although the embodiments have been described in connection with the limited embodiments and the drawings, those skilled in the art may modify and change the embodiments in various ways from the description. For example, proper results may be achieved although the aforementioned descriptions are performed in order different from that of the described method and/or the aforementioned elements, such as the system, configuration, device, and circuit, are coupled or combined in a form different from that of the described method or replaced or substituted with other elements or equivalents.

Accordingly, other implementations, other embodiments, and the equivalents of the claims fall within the scope of the claims.

What is claimed is:

1. An implantable device comprising an implantable sensor configured to form a magnetic dipole moment in one direction outside a body within the body wherein the implantable device is configured to be inserted into the body and to measure biometric information by using the implantable sensor, and wherein the implantable sensor has a triple folded loop structure in which one port feeding and a folded double loop have been merged.

2. The implantable device of claim 1, wherein the port feeding and the folded double loop are merged to form magnetic dipole resonance through single feeding.

3. The implantable device of claim 1, wherein a current at a top of the triple folded loop structure and a current at a bottom of the triple folded loop structure are offset to form sub-radiative resonance by a vertical symmetry shape of the triple folded loop structure.

4. The implantable device of claim 1, wherein:
  a first side of the port feeding is connected to a first side at a top of a first folded loop of the folded double loop,
  a second side of the port feeding is connected to a first side at a top of a second folded loop of the folded double loop, and
  a second side at a bottom of the first folded loop and a second side at a bottom of the second folded loop are connected.

5. The implantable device of claim 1, wherein the triple folded loop structure is implemented in a printed circuit board (PCB).

6. The implantable device of claim 1, further comprising a power source for applying a current to the implantable sensor,
- wherein a current is induced into an external sensor outside the body, which has a loop structure, by a magnetic field that is formed by a current applied from the power source to the implantable sensor, and
- a location of the implantable sensor is determined based on a size of the current induced into the external sensor.

7. An implantable device comprising an implantable sensor configured to form a magnetic dipole moment in one direction outside a body within the body, wherein the implantable device configured to be inserted into the body and measure biometric information by using the implantable sensor, and wherein:
- the implantable sensor has a triple folded loop structure having an oval structure, and a direction of the implantable sensor is determined based on a size of a current induced into an external sensor outside the body, which has a loop structure of an oval structure.

8. The implantable device of claim 7, wherein the biometric information is measured based on a change in magnetic dipole moment resonance according to a change in permittivity.

9. An implantable sensor having a triple folded loop structure in which one port feeding and a folded double loop have been merged.

10. The implantable sensor of claim 9, wherein the port feeding and the folded double loop are merged to form magnetic dipole resonance through single feeding.

11. The implantable sensor of claim 9, wherein a current at a top of the triple folded loop structure and a current at a bottom of the triple folded loop structure are offset to form sub-radiative resonance by a vertical symmetry shape of the triple folded loop structure.

12. The implantable sensor of claim 9, wherein:
- a first side of the port feeding is connected to a first side at a top of a first folded loop of the folded double loop,
- a second side of the port feeding is connected to a first side at a top of a second folded loop of the folded double loop, and
- a second side at a bottom of the first folded loop and a second side at a bottom of the second folded loop are connected.

13. The implantable sensor of claim 9, wherein each of the port feeding and the folded double loop has an oval shape.

* * * * *